(12) United States Patent
Mourier et al.

(10) Patent No.: US 9,346,894 B2
(45) Date of Patent: May 24, 2016

(54) POLYSACCHARIDES COMPRISING TWO ANTITHROMBIN III-BINDING SITES, PREPARATION THEREOF AND USE THEREOF AS ANTITHROMBOTIC MEDICAMENTS

(75) Inventors: Pierre Mourier, Paris (FR); Christian Viskov, Paris (FR)

(73) Assignee: SANOFI, Paris (FR)

( * ) Notice: Subject to any disclaimer, the term of this patent is extended or adjusted under 35 U.S.C. 154(b) by 165 days.

(21) Appl. No.: 14/111,300

(22) PCT Filed: Apr. 11, 2012

(86) PCT No.: PCT/IB2012/051768
§ 371 (c)(1),
(2), (4) Date: Oct. 11, 2013

(87) PCT Pub. No.: WO2012/140580
PCT Pub. Date: Oct. 18, 2012

(65) Prior Publication Data
US 2014/0031316 A1    Jan. 30, 2014

(30) Foreign Application Priority Data
Apr. 11, 2011    (FR) ...................................... 11 53116

(51) Int. Cl.
*C08B 37/00*    (2006.01)
*A61K 31/727*    (2006.01)
*G01N 30/86*    (2006.01)
*B01D 15/34*    (2006.01)
(Continued)

(52) U.S. Cl.
CPC ........... *C08B 37/0075* (2013.01); *A61K 31/727* (2013.01); *A61K 45/06* (2013.01); *B01D 15/34* (2013.01); *B01D 15/363* (2013.01); *B01D 15/3823* (2013.01); *B01D 15/1878* (2013.01); *Y10T 436/143333* (2015.01)

(58) Field of Classification Search
CPC ............. C08B 37/0075; A61K 31/727; G01N 30/8679
See application file for complete search history.

(56) References Cited

U.S. PATENT DOCUMENTS 8,003,623 B2    8/2011    Biberovic et al.
8,071,570 B2    12/2011    Viskov et al.

FOREIGN PATENT DOCUMENTS

WO    WO 2004/033503 A1    4/2004
WO    WO 2007/012754 A1    2/2007

OTHER PUBLICATIONS

Google machine translation of WO 2004/033503 A1, https://www.google.com/patents/, accessed online on Aug. 18, 2015.*

(Continued)

*Primary Examiner* — Jonathan S Lau
(74) *Attorney, Agent, or Firm* — Scully Scott Murphy and Presser

(57) ABSTRACT

The invention relates to sulphated polysaccharides which have the general structure of the constituent polysaccharides of heparin and which have a molecular weight of less than 8000 Daltons, comprising two antithrombin III-binding hexasaccharide sequences corresponding to formula (I) in which: R1 represents an OH group when the hexasaccharide of formula (I) is located at the reducing end of the polysaccharide, or else R1 represents a bond with another saccharide unit of said polysaccharide; R2 represents a hydrogen atom when the hexasaccharide of formula (I) is located at the non-reducing end of the polysaccharide, in which case the bond between carbon atoms 4 and 5 of the first saccharide unit of said hexasaccharide is a double bond, or else R2 represents a bond with another saccharide unit of said polysaccharide, in which case the bond between carbon atoms 4 and 5 of the first saccharide unit is a single bond. Preparation thereof, use thereof as antithrombotic medicaments, and also use thereof in a method for analyzing a sample of a heparin derivative.

21 Claims, 9 Drawing Sheets

Figure 1:
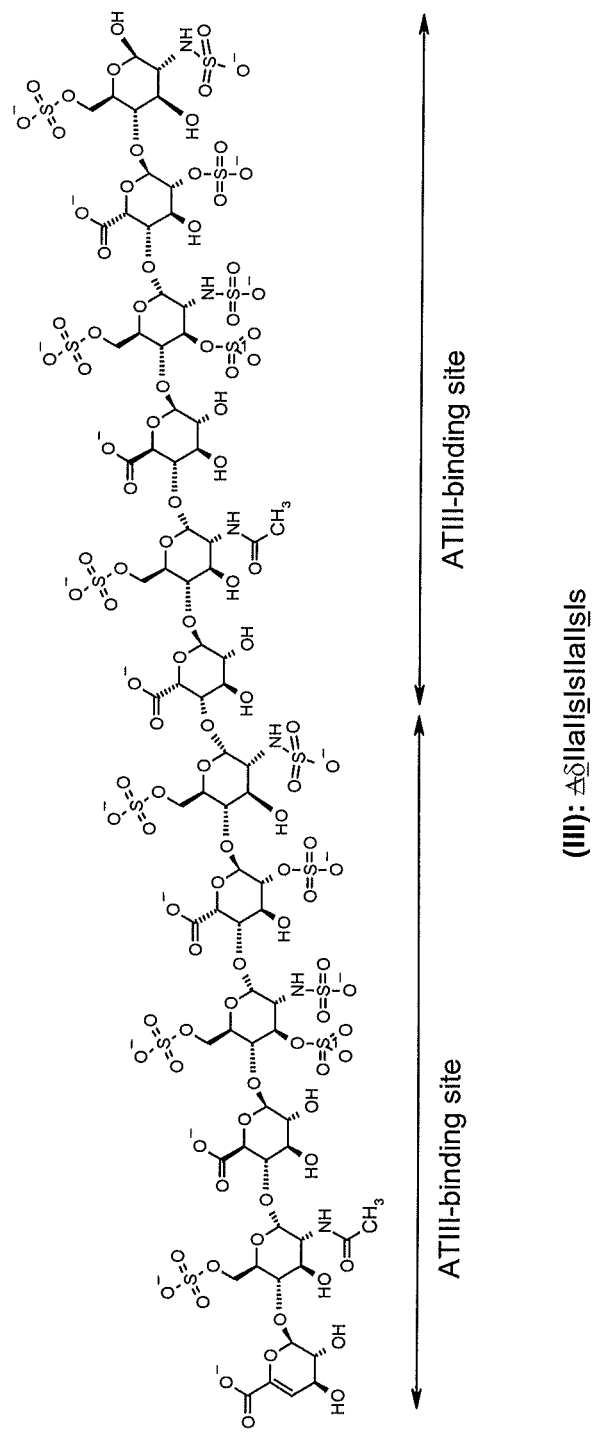

(51) Int. Cl.
  *B01D 15/36* (2006.01)
  *B01D 15/38* (2006.01)
  *A61K 45/06* (2006.01)
  *B01D 15/18* (2006.01)

(56) References Cited

OTHER PUBLICATIONS

Noti et al., Chemistry & Biology, 2005, 12, p. 731-756.*
Hook, M. et al., Anticoagulant Activity of Heparin: Separation of High-Activity and Low-Activity Heparin Species by Affinity Chromatography on Immobilized Antithrombin, FEBS Letters, (Jul. 1, 1976), vol. 66, No. 1, pp. 90-93.
Jordan, R.E. et al., Heparin with Two Binding Sites for Antithrombin or Platelet Factor 4, The Journal of Biological Chemistry, (Jan. 10, 1982), vol. 257, Issue 10, pp. 400-406.
Linhardt, R. J. et al., Structure and Activity of a Unique Heparin-derived Hexasaccharide, The Journal of Biological Chemistry, (Nov. 5, 1986), vol. 261, No. 31, pp. 14448-14454.
International Search Report dated Aug. 3, 2012 issued in PCT/IB2012/051768.

* cited by examiner

POLYSACCHARIDES COMPRISING TWO ANTITHROMBIN III-BINDING SITES, PREPARATION THEREOF AND USE THEREOF AS ANTITHROMBOTIC MEDICAMENTS

The present invention relates to polysaccharides comprising two antithrombin III-binding sites, to the process for preparing same and to the use thereof as antithrombotic medicaments.

Heparin is well known for its anticoagulant properties, mediated by the activation of antithrombin III (ATIII), a physiological inhibitor of coagulation. It has been used clinically since the 1930s for preventing and treating vein thrombosis.

Since the end of the 1970s, the activity of heparin has been more clearly understood through structural studies of its components, obtained by depolymerization and fractionation. It has thus been possible to show that some of the polysaccharide chains present in heparin have an antithrombin-binding site and that the latter consists of an oligosaccharide sequence CDEFGH containing six sugars (M. Petitou et al., Biochimie, 2003, vol. 85, p. 83-89):

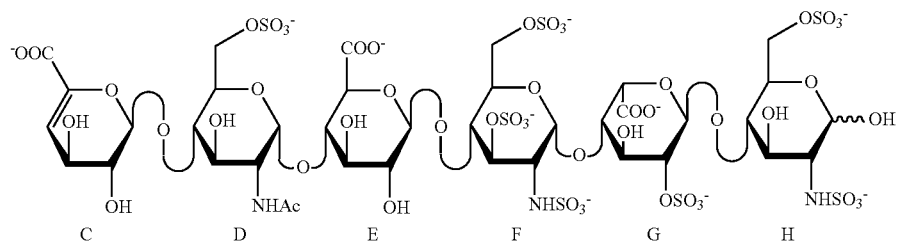

The hypothesis of a minimum sequence of five sugars, DEFGH, allowing binding to antithrombin, has also been proposed, leading to the development and marketing of fondaparinux, which is a synthetic pentasaccharide that is a selective inhibitor of factor Xa (structure below):

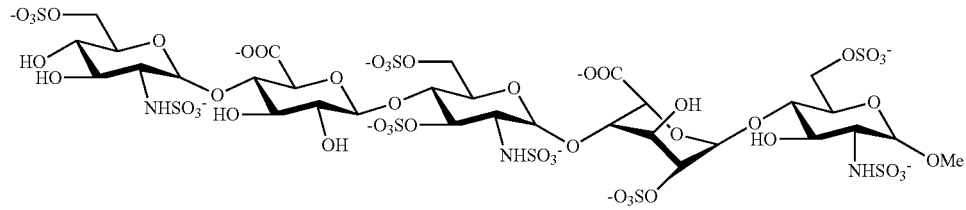

Moreover, products derived from heparin, low-molecular-weight heparins (LMWHs), have been developed since the 1970s. These products are obtained by chemical or enzymatic depolymerization from heparin. They consist of complex mixtures of polysaccharides and have a greater specificity of action than heparin on the various factors involved in the coagulation cascade, making it possible in particular to reduce the risks of haemorrhages inherent in heparin.

The inventors have now found a novel approach for identifying compounds with antithrombotic properties. Starting from heparin derivatives, original separation techniques have made it possible to isolate polysaccharides which have particular structures, unknown to date in sugar chemistry, which have excellent antithrombotic properties and which can therefore be used therapeutically.

A subject of the invention is sulphated polysaccharides which have the general structure of the constituent polysaccharides of heparin and which have a molecular weight of less than 8000 Daltons, characterized in that they comprise two ATIII-affinity sites.

The polysaccharides according to the invention advantageously comprise two ATIII-binding hexasaccharide sequences. Thus, they may be denoted as "double site" compounds in the remainder of the text.

The expression "sulphated polysaccharides which have the general structure of the constituent polysaccharides of heparin" is intended to mean compounds comprising a series of saccharide units such as those present in heparin. Thus, the polysaccharides according to the invention are composed of a series of disaccharide units, which may be identical to or different from one another, comprising a D-glucosamine and a uronic acid linked in the 1→4 position.

The expression "ATIII-binding hexasaccharide sequence" is intended to mean more specifically the hexasaccharide corresponding to formula (I):

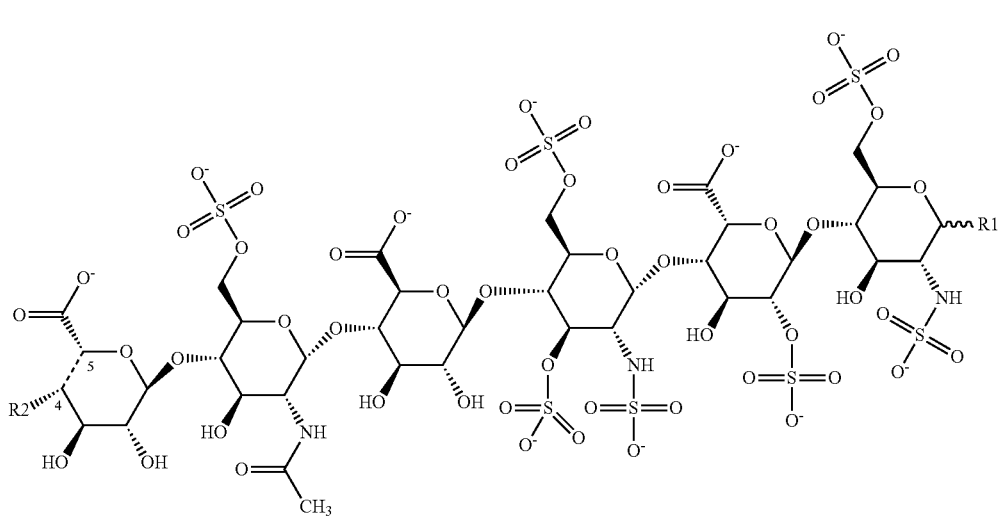

in which:
the bond represented as a dashed line between carbon atoms 4 and 5 of the first saccharide unit is either a single bond or a double bond,
the wavy line (for the R1 group) denotes a bond located either below or above the plane of the pyranose ring of the glucosamine unit to which R1 is attached,
R1 represents an OH group when the hexasaccharide of formula (I) is located at the reducing end of the polysaccharide, or else R1 represents a bond with another saccharide unit of said polysaccharide, in which case the bond is situated above the plane of the pyranose ring of the glucosamine unit to which R1 is attached,
R2 represents a hydrogen atom when the hexasaccharide of formula (I) is located at the non-reducing end of the polysaccharide, in which case the bond between carbon atoms 4 and 5 of the first saccharide unit of said hexasaccharide is a double bond, or else R2 represents a bond with another saccharide unit of said polysaccharide, in which case the bond between carbon atoms 4 and 5 of the first saccharide unit of said hexasaccharide is a single bond.

The polysaccharides according to the invention are in acid form or in salified form, in particular in the form of any one of the pharmaceutically acceptable salts thereof. In the acid form, the —COO⁻ and —SO₃⁻ functions are respectively in the —COOH and —SO₃H forms. The expression "pharmaceutically acceptable salt of the compounds of the invention" is intended to mean a compound in which one or more of the —COO⁻ and/or —SO₃⁻ function(s) is (are) ionically bonded to a pharmaceutically acceptable cation, for example the Na⁺ cation.

The structure of the polysaccharides according to the invention is surprising, in the sense that no polysaccharide structure of this size comprising two ATIII-affinity sites has been reported in the literature to date.

It is well established for those skilled in the art that the polysaccharide chains interact with antithrombin when the specific affinity sequence CDEFGH previously described is present in the macromolecule. All the representations in this field illustrate the interaction of a heparin chain with an antithrombin protein and the inhibition, by this complex, of factor Xa, or even of factor IIa if the chain length is greater than 18 saccharides (see, for example, the article by M. Petitou in L→actualité Chimique [Chemical News], November 1999, pages 18-21).

The presence of two antithrombin-binding sites has been demonstrated by R. Jordan et al. (Journal of Biological Chemistry, 1982, vol. 257, no. 1, p. 400-406) in high-molecular-weight heparin fractions, namely of approximately 18 000 to 22 000 Daltons. On the other hand, analysis of the low-molecular-weight fractions (approximately 6 000 to 8 000 Daltons) have demonstrated the presence of a single site of interaction with antithrombin.

Thus, the very idea that a low-molecular-weight polysaccharide can interact with at least two antithrombin proteins, and as a result have at least two possibilities of inhibiting factor Xa, is totally unexpected, as are the subsequent biological effects linked to these novel sequences.

The original structures of the "double site" oligosaccharides according to the present invention thus open up new possibilities for a therapeutic use, by virtue of their powerful antithrombotic properties, as will be subsequently detailed.

Among the compounds according to the invention, mention may be made of the polysaccharides which comprise between 12 and 22 saccharide units. They may be represented by formula (II):

in which:
the A, B and C units, which may be identical to or different from one another, represent disaccharide sequences. The disaccharide sequences advantageously comprise a uronic acid and a D-glucosamine, which are optionally substituted (for example, sulfated or acylated). The A, B and C disaccharide units are either present, or absent, which is indicated by the subscripts d, f and g;
the units of formula (I) represent hexasaccharide units, as defined previously (see formula (I) above),
the subscripts d, f and g each represent an integer equal to 0 (in which case the A, B or C unit to which they refer is absent) or comprised between 1 and 5, on the condition that the sum of the integers d, f and g is comprised between 0 and 5.

Among the compounds according to the invention, mention may more particularly be made of the polysaccharides which comprise 12 or 14 saccharide units; they may be represented by formula (II bis):

in which:
the A, B and C units, which may be identical to or different from one another, represent disaccharide sequences. The disaccharide sequences advantageously comprise a uronic acid and a D-glucosamine, which are optionally substituted (for example, sulfated or acylated). The A, B and C disaccharide units are either present, or absent, which is indicated by the subscripts n, m and k;
the units of formula (I) represent hexasaccharide units, as defined previously (see formula (I) above),
the subscripts n, m and k each represent an integer equal to 0 (in which case the A, B or C unit to which they refer is absent) or to 1 (in which case the A, B or C unit to which they refer is present), on the condition that, when one of the subscripts n, m or k is equal to 1, then the other two subscripts are equal to 0.

Among the compounds according to the invention, mention may be made of a polysaccharide which comprises 12 saccharide units (dodecasaccharide). It is a compound of formula (II bis) above in which n=m=k=0. It advantageously corresponds to formula (III) according to FIG. 1 hereinafter and is in acid form or in salified form, as previously described.

Figure 2:
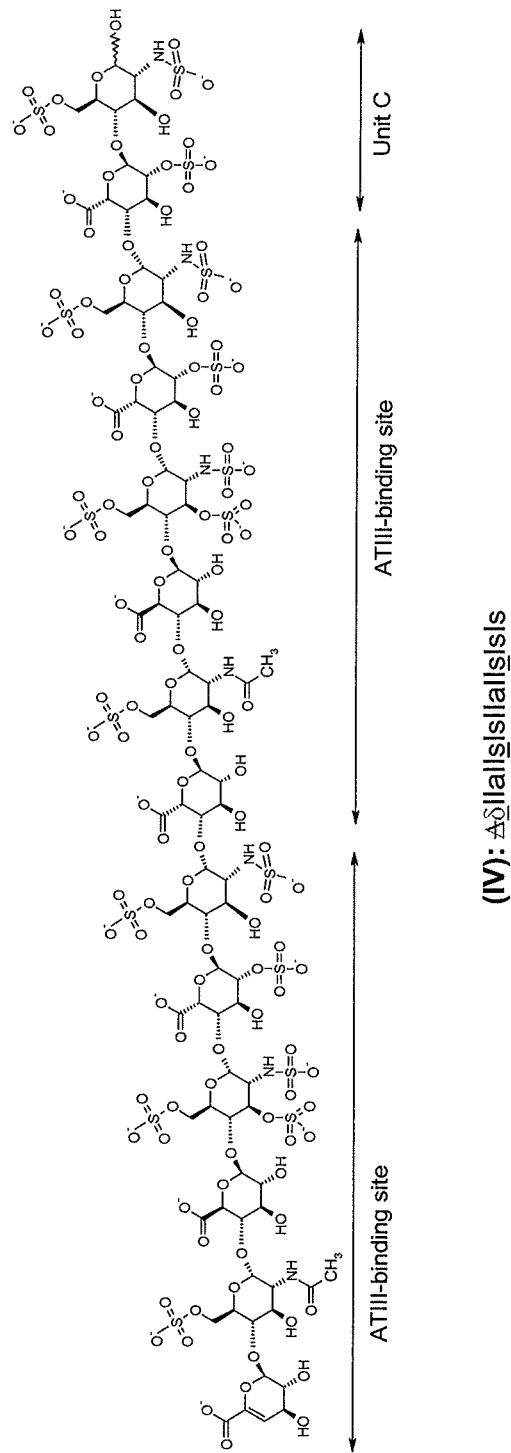
Figure 3:
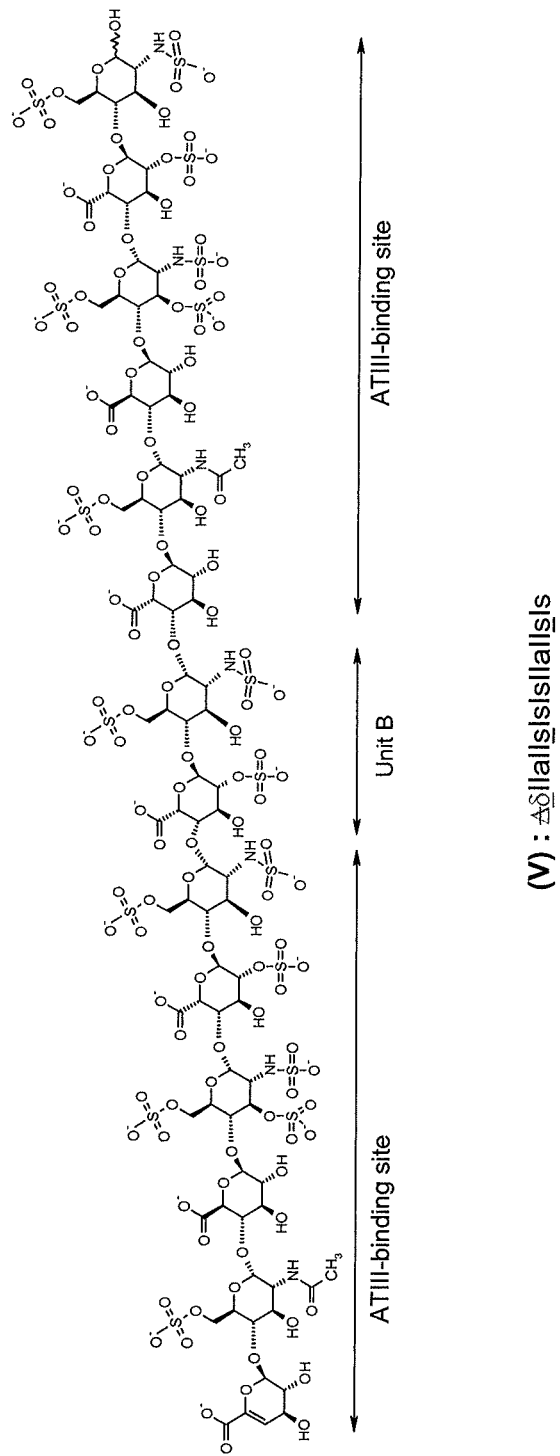
Figure 4:
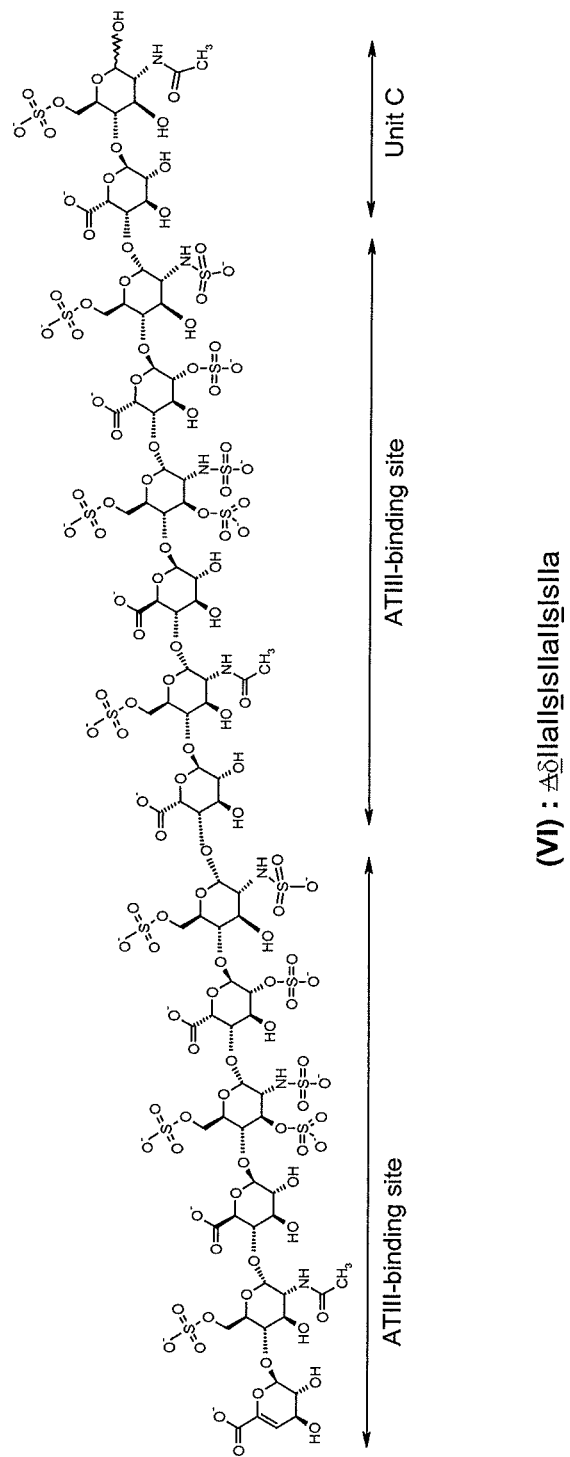

Other polysaccharides according to the invention may comprise 14 saccharide units (tetradecasaccharides). They are compounds of formula (II bis) above in which one of the subscripts among n, m and k is equal to 1, the other two subscripts being equal to 0. They may, for example, correspond to formulae (IV), (V) and (VI) according to FIGS. 2, 3 and 4, respectively, and in which the wavy line denotes a bond located either below or above the plane of the pyranose cycle of the glucosamine unit. Such polysaccharides are in acid form or in salified form, as previously described.

The polysaccharides according to the invention can be obtained from heparin derivatives using orthogonal (combined) separation techniques for separating the constituent polysaccharides of these mixtures according to their sizes, their charges and their affinities for ATIII. Gel permeation chromatography, high performance liquid chromatography and ATIII affinity chromatography techniques are therefore used. These techniques are combined with one another in any envisageable order.

The gel permeation chromatography (GPC) can be carried out on columns packed with Bio Gel P30 (Bio-Rad) with 0.2 M $NaCla_4$ as eluent circulating at a flow rate preferentially between 80 and 100 ml/h. The fractions are desalted on a column packed with Sephadex G10.

The ATIII affinity chromatography can be carried out on columns packed with AT-Sepharose. The stationary phase is prepared by coupling human AT (antithrombin) (1 g, Biomed) to CNBr-activated Sepharose 4B (Sigma). The methodology used to prepare the AT column is based on the teachings of Höök et al. (FEBS Letters, 1976, 66(1), 90-3) and the patent application WO 2007/012754. The affinity column is eluted using an NaCl gradient. The low-affinity fraction is eluted from the column with a 0.25 M NaCl solution buffered at pH 7.4 with 1 mM Tris. The high-affinity fractions are eluted using a step gradient of NaCl concentration. The eluate is monitored by conductimetry and absorptiometry in the UV range at 232 nm.

The high performance liquid chromatography (HPLC) uses the CTA-SAX technique (dynamic or strong anion exchange chromatography with cetyltrimethylammonium). The semi-preparative CTA-SAX columns (for example 250× 22 mm) are grafted as described by Mourier, P. A. J. and Viskov, C. in Analytical Biochemistry, 2004, 332, 299-313, on columns packed with Hypersil betabasic C18 (5 µm). The grafting of the column is carried out as for the analytical columns, by infusion of a solution of cetyltrimethylammonium hydrogen sulphate (CTA) in a water/methanol mixture. The mobile phases are aqueous solutions of sodium methanesulphonate, at concentrations ranging between 0 and 2.5 M. The pH is adjusted to 2.5 by adding dilute methanesulfonic acid.

The various polysaccharides according to the invention can be isolated according to the order in which they are eluted in liquid chromatography: polysaccharides of the same size can be eluted at distinct retention times according to their chemical nature, the presence of various charges and substituents along the polysaccharide backbone influencing the order in which they exit at the end of the chromatography. The techniques described in Analytical Biochemistry (ibid), using sequencing of the oligosaccharides after partial depolymerization with heparinases, can be used for identifying the polysaccharides eluted at the end of the CTA-SAX, as can any other method known to those skilled in the art, such as identification by proton NMR.

The fractions collected at the end of the CTA-SAX are neutralized, purified and desalted by gel filtration, for example on Sephadex G10 after a preliminary treatment on Mega Bond Elut C18 cartridges (Varian).

In the case of more difficult separations, smaller columns (150×10 mm) packed with Hypersil Betabasic C18 (3 µm) grafted with CTA as described above, can be used. The mobile phases correspond to those used in the analytical systems, which are aqueous solutions of ammonium methanesulphonate, at concentrations between 0 and 2 M. The rate is, for example, 4 ml/min.

A final separation step can be carried out on a semi-preparative anion exchange column, such as an AS11 column (Dionex). The mobile phase is, for example, made up as follows: solvent A: water; solvent B: 1M $NaClO_4$. The elution gradient may be the following: T=0 min: % B=1; T=60 min: % B=80 with a flow rate of 20 ml/min. The detection is carried out in the UV range at 232 nm. The fractions selected are desalted by gel filtration, for example on a Sephadex G10 column.

In order to obtain the polysaccharides according to the present invention, the abovementioned separation techniques are applied to a very particular LMWH, obtained by depolymerization of a quaternary ammonium salt of the benzyl ester of heparin by means of a phosphazene base. Such an LMWH is currently under clinical development for the prevention of vein thrombosis: it is semuloparin, representing a new generation of hemisynthetic LMWHs, having an average molecular weight of from 2000 to 3000 Daltons and a new antithrombotic profile, resulting from a high anti-factor Xa (anti-FXa) activity and a residual anti-factor IIa (anti-FIIa) activity. Its properties and examples for its preparation are described, for example, in the Journal of Thrombosis and Haemostasis, 2009, vol. 7, 1143-1151. With regard to its particular properties, in particular its ultra low average molecular weight, semuloparin is defined in the category of ultra-low-molecular-weight heparins (ULMWHs).

Surprisingly, the polysaccharides according to the invention have been obtained from an ULMWH as described for example in the patent application WO 2004/033503, in particular from semuloparin: to date, such polysaccharides have never been identified, nor isolated from the other low-molecular-weight or ultra-low-molecular weight heparins currently known, such as enoxaparin. Their structures, comprising a double ATIII-binding site, are therefore completely unexpected for those skilled in the art and innovative in the heparin derivative field.

A subject of the invention is the polysaccharides previously described in isolated form.

A subject of the invention is also the polysaccharides previously described in the form of mixtures with other polysaccharides, whatever they are. In particular, a subject of the invention is a low-molecular-weight or ultra-low-molecular-weight heparin which comprises one or sulphated polysaccharides having the general structure of the constituent polysaccharides of heparin and comprising two antithrombin-III-affinity sites, such as the polysaccharides (I) previously described.

According to the present invention, the term "Low-Molecular-Weight Heparin" (LMWH) is intended to mean a mixture of sulphated polysaccharides which is obtained from heparin and has an average molecular weight of less than 8000 Daltons, as defined in the European Pharmacopoeia 6.0 (01/2008:0828, 2041-2043). The term "Ultra-Low-Molecular-Weight Heparin" (ULMWH) or "Very Low Molecular Weight Heparin" (VLMWH) is intended to mean a mixture having an average molecular weight of less than 4000 Daltons, more particularly less than or equal to 3000 Daltons.

A subject of the invention is also a low-molecular-weight heparin or an ultra-low-molecular-weight heparin, in particular semuloparin, which comprises the polysaccharide of formula (III) as defined above (dodecasaccharide), in a content preferentially between 1 and 2.5% expressed as percentage area relative to the ATIII-affinity dodecasaccharide fraction. The term "percentage area" is intended to mean the percentage of the area under the curve (AUC) obtained by HPLC chromatographic analysis.

In order to assay the content of double-site dodecasaccharide of formula (III) in the dodecasaccharide fraction of semuloparin, the methodology used preferentially involves three chromatographic steps, as previously described. By way of example, the assay was carried out using the following three sequences: the first step is an isolation of the dodecasaccharide fraction by GPC (Gel Permeation Chromatography); the second step involves running the previously isolated dodecasaccharide fraction through ATIII-affinity chromatography in order to split it into an affinity fraction and a nonaffinity fraction; finally, in a last step, the affinity fraction is chromatographed by HPLC in order to estimate the percentage of the double-site compound, as a percentage area relative to the ATIII-affinity dodecasaccharide fraction.

The particularity of the polysaccharides of the formula (I) according to the invention makes it possible to characterize them as tracers for LMWHs and ULMWHs which may contain them. More specifically, since the polysaccharides of formula (I) according to the invention have been detected in semuloparin, it is possible to analyse a sample of a heparin derivative and to conclude therefrom, among other relevant tests, whether or not it is indeed semuloparin by verifying the presence or the absence of said polysaccharides of formula (I) and, optionally, to verify whether or not the content of said polysaccharides corresponds to the expected amounts. Steps for verifying the nature of a sample of a heparin derivative (semuloparin or not) and whether it conforms to a standard sample of semuloparin (presence of the tracer compounds in the required amounts) are therefore included in the scope of the invention.

Thus, a subject of the invention is also a method for analysing a sample of a heparin derivative, in particular semuloparin, comprising the following steps:
a) subjecting the test sample to orthogonal separation steps as previously defined, comprising a step of isolating the dodecasaccharide fraction and/or the tetradecasaccharide fraction of said sample,
b) detecting the presence or absence of one or more sulphated polysaccharides of formula (III), (IV), (V) or (VI), as defined above, in said dodecasaccharide and/or tetradecasaccharide fractions,
c) optionally, quantifying the content of one or more of said sulphated polysaccharides in the test sample.

Such a method may have the objective of verifying whether or not the test sample conforms to a standard sample of an LMWH or a ULMWH, in particular semuloparin. Thus, said method may, in addition, comprise a step d) which enable to conclude that the test sample conforms to said standard sample when step b) makes it possible to detect the presence of one or more of the sulphated polysaccharides mentioned in step b) and, optionally, when step c) makes it possible to quantify the content of said polysaccharide(s) in prespecified contents of said standard sample. Conversely, when step b) does not make it possible to detect the presence of at least one of the sulphated polysaccharides mentioned in step b) or when step c) results in the quantification of said polysaccharide(s) outside the prespecified contents for the standard sample, then it can be concluded that the test sample does not conform to the standard sample.

Thus, a subject of the invention is also a method for analysing a sample of a heparin derivative, in particular semuloparin, comprising the following steps:
a) subjecting the test sample to orthogonal separation steps as defined previously, comprising a step of isolating the dodecasaccharide fraction and/or the tetradecasaccharide fraction of said sample,
b) detecting the presence or absence of one or more sulphated polysaccharides of formula (III), (IV), (V) or (VI), as defined above, in said dodecasaccharide and/or tetradecasaccharide fractions,
c) optionally, quantifying the content of one or more of said sulphated polysaccharides in the test sample,
d) concluding that the test sample conforms to a standard sample when step b) makes it possible to detect the presence of one or more of the sulphated polysaccharides of formula (III), (IV), (V) or (VI), and, optionally, when step c) makes it possible to quantify the content of said polysaccharide(s) in prespecified contents of said standard sample.

Another subject of the invention is a method for analysing a sample of a heparin derivative, in particular semuloparin, comprising the following steps:
a) subjecting the test sample to orthogonal separation steps as defined previously, comprising a step of isolating the dodecasaccharide and/or the tetradecasaccharide fraction of said sample,
b) detecting the presence or absence of one or more sulphated polysaccharides of formula (III), (IV), (V) or (VI), as defined above, in said dodecasaccharide and/or tetradecasaccharide fractions,
c) optionally, quantifying the content of one or more of said sulphated polysaccharides in the test sample,
d) concluding that the test sample does not conform to a standard sample when step b) does not make it possible to detect the presence of at least one of the sulphated polysaccharides of formula (III), (IV), (V) or (VI) and, optionally, when step c) results in the quantification of said polysaccharide(s) outside the prespecified contents for the standard sample.

The standard sample mentioned above is advantageously a sample of semuloparin.

In step b) of the methods for analysing a sample of a heparin derivative that are described above, it is advantageously the sulphated polysaccharide of formula (III) which is sought, this being in the dodecasaccharide fraction of the sample. Thus, step a) advantageously comprises a step of providing a dodecasaccharide fraction isolated from the test sample, and therefore resides in subjecting the test sample to orthogonal separation steps as previously defined, comprising a step of isolating the dodecasaccharide fraction of said sample. Consequently, step b) advantageously comprises a step for detecting the presence or absence of the sulphated polysaccharide of formula (III) in said dodecasaccharide fraction of the test sample. As for step c), it can therefore advantageously comprise a step for quantifying the content of the polysaccharide (III) in the test sample. Then, step d) can therefore make it possible to conclude that the test sample conforms when step b) makes it possible to detect the presence of the polysaccharide (III) and, optionally, when step c) makes it possible to quantify the content of said polysaccharide (III) in a range of from 1 to 2.5%, as a percentage area relative to the ATIII-affinity dodecasaccharide fraction. The converse situation, i.e. when step b) does not make it possible to detect the presence of the polysaccharide (III) and, optionally, when step c) does not make it possible to quantify said polysaccharide (III) in the above contents, makes it possible to conclude that the test sample does not conform to a standard sample of semuloparin.

The methods for analysing a sample of a heparin derivative that are described above can also comprise a step e) for selecting a batch as a consequence of the prior analysis steps a), b), optionally c), and d). Such a batch selection is useful during the clinical development of a heparin derivative or during the marketing of such a product, in that it can be included among the numerous tests necessary for the release of a batch, for example with the aim of its clinical use, particularly in humans. Thus, the method of analysis according to the invention may be a method of monitoring or testing the production of batches of a heparin derivative, in particular of semuloparin.

Another subject of the invention is a process for analyzing a sample of a heparin derivative, in particular of semuloparin, comprising the following steps:
  a) subjecting the test sample to orthogonal separation steps as defined previously, comprising a step of isolating the dodecasaccharide fraction and/or the tetradecasaccharide fraction of said sample,
  b) detecting the presence or absence of one or more sulphated polysaccharides of formula (III), (IV), (V) or (VI), as defined above, in said dodecasaccharide and/or tetradecasaccharide fractions,
  c) optionally, quantifying the content of one or more of said sulphated polysaccharides in the test sample;
  wherein detection of the presence of one or more of the sulphated polysaccharides of formula (III), (IV), (V) or (VI) in step b), and, optionally, the amount of said polysaccharide(s) quantified in step c) being within the prespecified content of said polysaccharide(s) of the standard semuloparin sample, indicates that the test sample conforms to the standard sample;
  and wherein detection of the absence of one or more of the sulphated polysaccharides of formula (III), (IV), (V) or (VI) in step b) and, optionally, the amount of said polysaccharide(s) quantified in step c) being outside the prespecified contents for the standard sample indicates that the test sample does not conform to the standard sample.

The following examples describe in detail the preparation and the assaying of certain compounds in accordance with the invention. These examples are not limiting and merely indicate the present invention.

Figure 5:
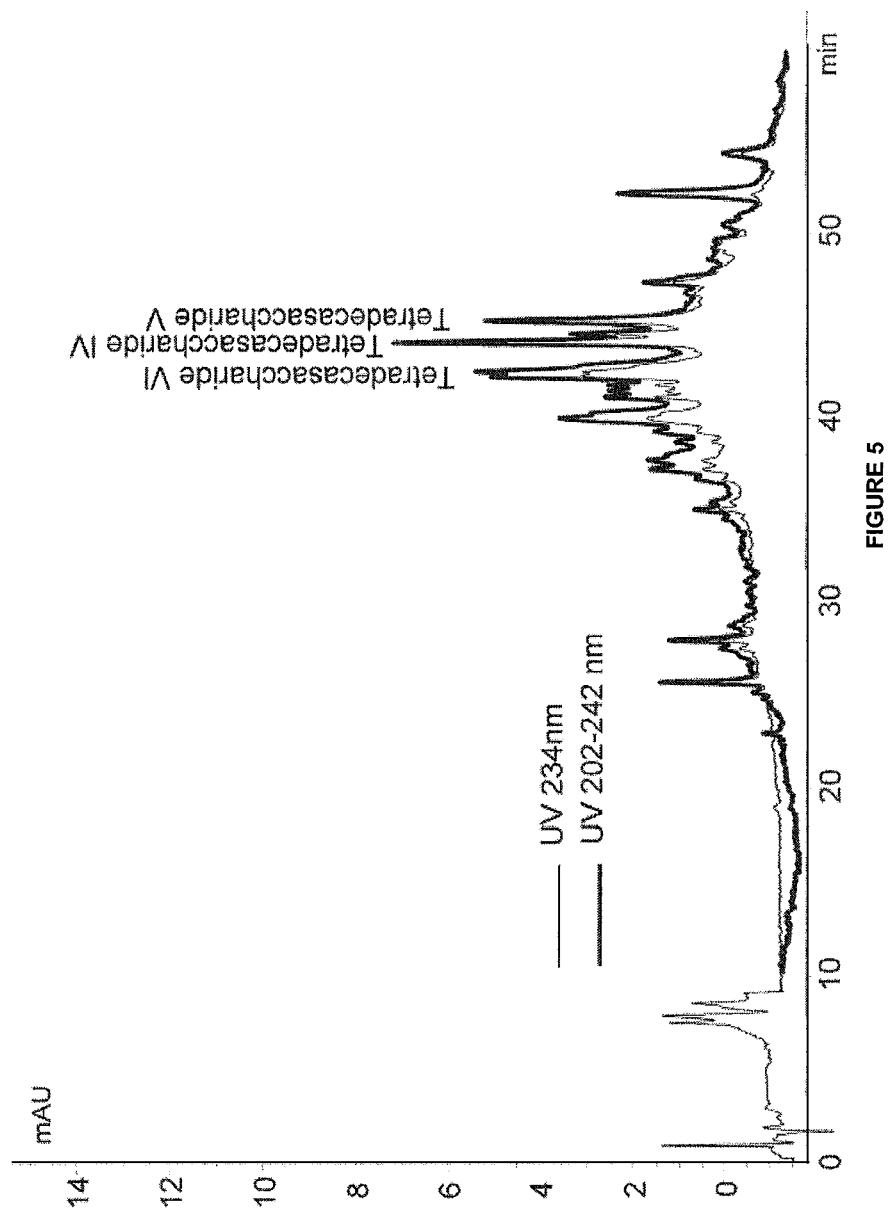
Figure 6:
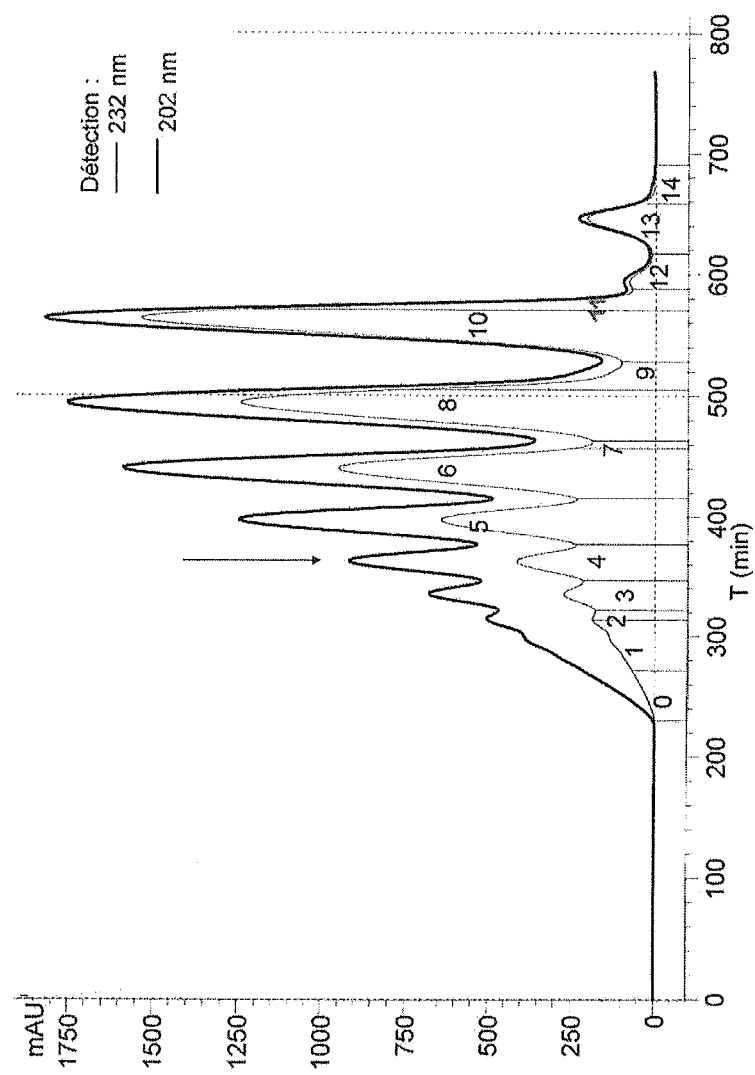
Figure 7:
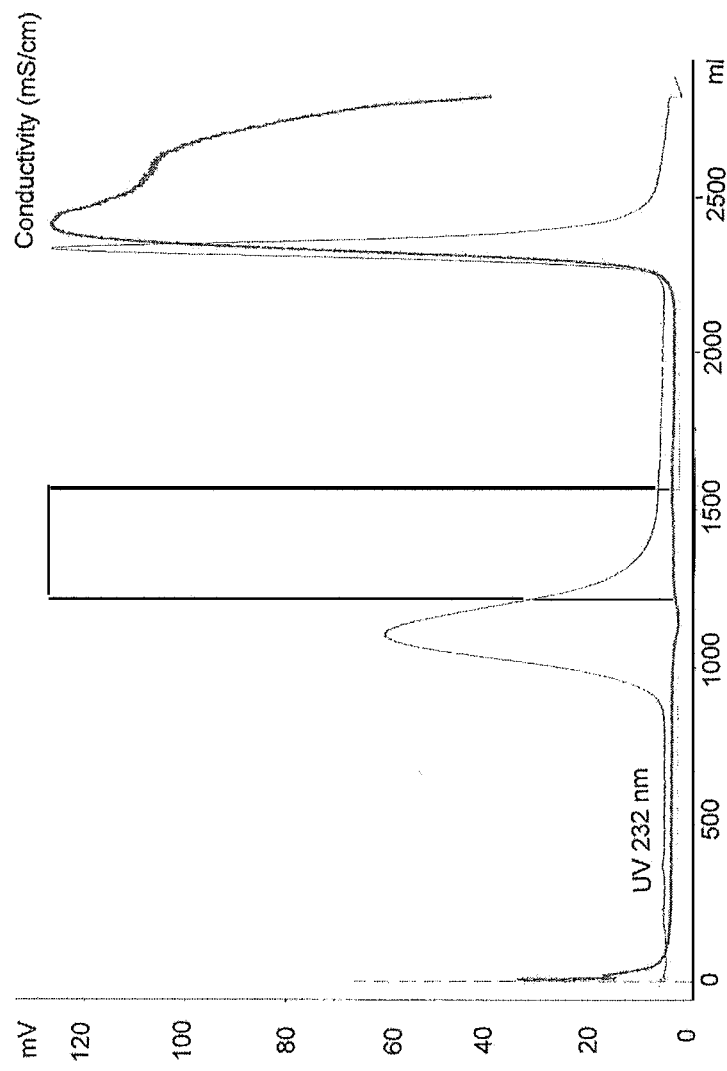
Figure 8:
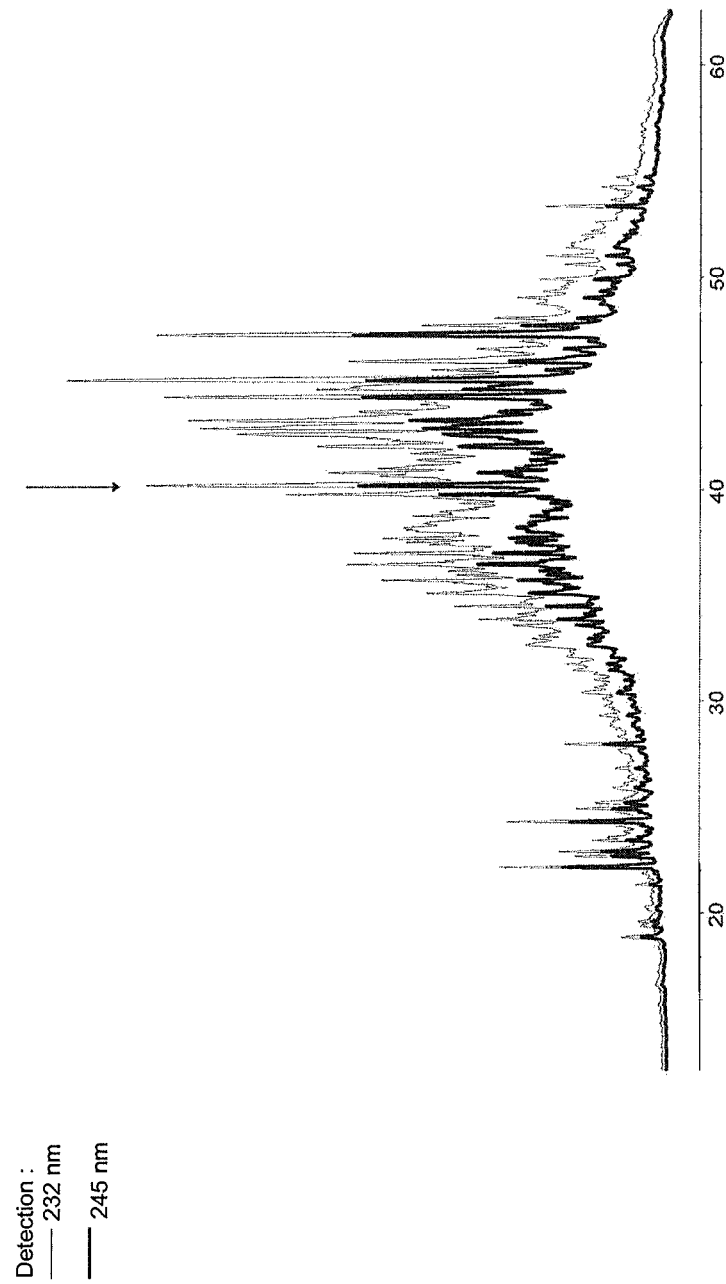
Figure 9:
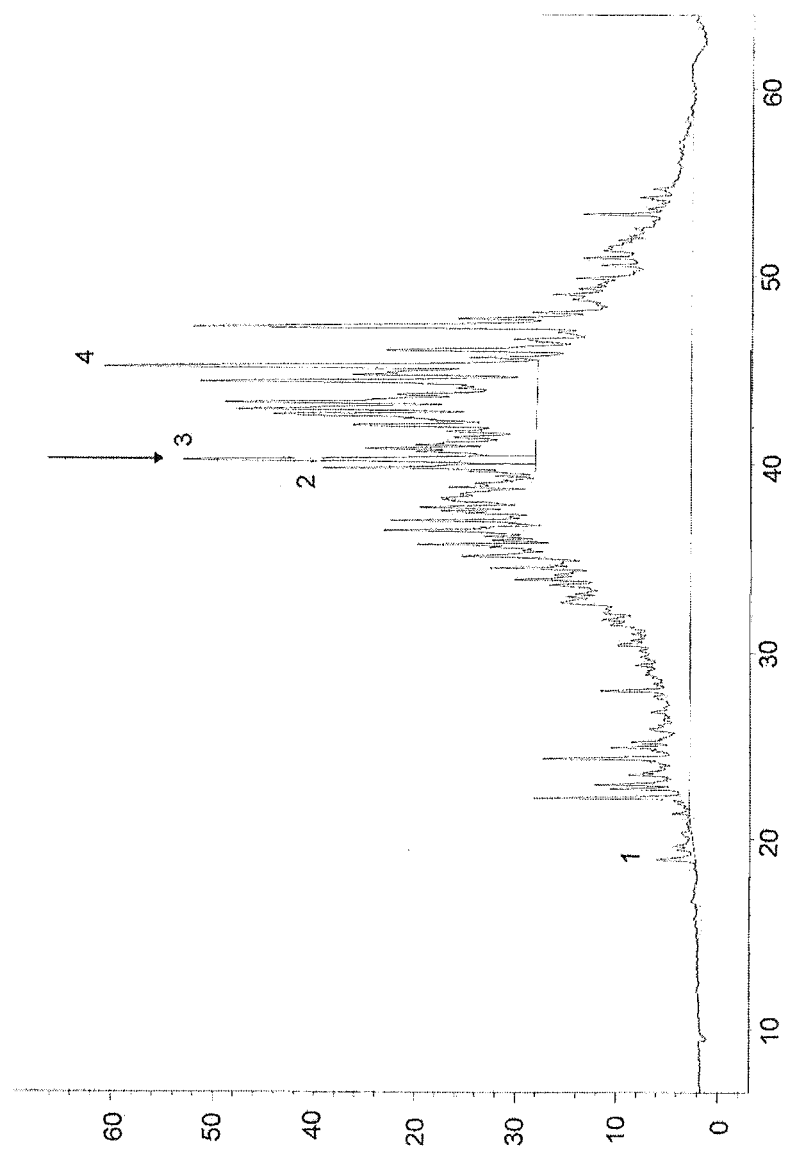

The appended figures are the following:

FIGS. 1, 2, 3 and 4: structures of the compounds (III), (IV), (V) and (VI), respectively, according to the invention;

FIG. 5: analytical CTA-SAX chromatogram of the tetradecasaccharide fraction obtained after GPC, ATIII chromatography and anion exchange chromatography (examples 3, 4 and 5 below);

FIG. 6: GPC chromatogram of a sample of semuloparin (example 6.1 below);

FIG. 7: chromatogram of antithrombin affinity of the dodecasaccharide fraction of a sample of semuloparin (example 6.2 below);

FIG. 8: chromatogram on a Waters Acquity BEH C18 UPLC column, of the affinity dodecasaccharide fraction of a sample of semuloparin (example 6.3 below);

FIG. 9: quantification of the double-site compound (III) on the chromatogram at 232 nm of the dodecasaccharide fraction chromatographed according to FIG. 8 (example 6.3 below).

EXAMPLE 1

Preparation of the Starting ULMWH

The ultra-low-molecular-weight heparin known under the name semuloparin (International Nonproprietary Name), and also under the laboratory code AVE5026 (Sanofi), is used as starting product for the preparation of the polysaccharides according to the present invention. Said heparin is prepared by depolymerization of a quaternary salt of the benzyl ester of the heparin in an organic medium by means of a phosphazene base (BEMP), conversion of the quaternary ammonium salt of the benzyl ester of the heparin depolymerized, into the sodium salt, saponification of the residual esters and final purification.

The quaternary ammonium salt of the benzyl ester of the heparin is advantageously the benzethonium salt.

The process for preparing AVE5026 thus comprises the following steps:
a) transalification of sodium heparin through the action of benzethonium chloride, so as to obtain benzethonium heparinate,
b) esterification of the benzethonium heparinate through the action of benzyl chloride, then treatment with an alcoholic solution of sodium acetate so as to obtain the sodium salt of the benzyl ester of the heparin,
c) transalification of the benzyl ester of heparin into a quaternary ammonium salt, using benzethonium salts,
d) depolymerization of the quaternary ammonium salt of the benzyl ester of the heparin by means of the method as defined above,
e) conversion of the quaternary ammonium (benzethonium) salt into the sodium salt,
f) saponification through the action of a base, such as sodium hydroxide,
g) purification, in particular through the action of an oxidizing agent such as aqueous hydrogen peroxide.

The reaction of step a) is advantageously carried out through the action of excess benzethonium chloride, on sodium heparin, at a temperature in the region of 15 to 25° C. During this step, the salt/sodium heparin molar ratio is advantageously between 3 and 4.

The starting heparin used is preferably a pig heparin. It can be pre-purified so as to reduce its dermatan sulphate content according to the process described in patent FR2663639.

The esterification of step b) is preferably carried out in a chlorinated organic solvent such as dichloromethane, at a temperature between 25 and 45° C., preferably between 30 and 40° C. The ester in benzethonium salt form is then recovered in sodium salt form by precipitation with 10% by weight sodium acetate in an alcohol such as methanol. Approximately 1 volume of alcohol per volume of reaction medium is generally used. The amount of benzyl chloride and the reaction time are adjusted so as to obtain a degree of esterification of between 50 and 100%, preferably between 70 and 90%. Preferentially, 0.5 to 1.5 parts by weight of benzyl chloride are used per part by weight of the benzethonium salt of the heparin. As for the reaction time, it is advantageously between 10 and 35 h.

The transalification of step c) is carried out by means of benzethonium chloride in an aqueous medium. Advantageously, the benzethonium chloride/sodium salt of the benzyl ester of the heparin mol ratio is between 2 and 3.

The depolymerization step is advantageously carried out in an aprotic solvent such as dichloromethane, with a water content of less than 0.6% by weight. Preferably, the water content in the reaction medium is less than 0.3%, more particularly less than 0.2%.

Advantageously, the phosphazene base/ester molar ratio is between 0.2 and 5, preferably between 0.6 and 2, and more particularly between 0.8 and 1.2. The use of an equimolar ratio is preferred.

Step e) is generally carried out by treating the reaction medium with an alcohol solution of sodium acetate, preferably in methanol, at a temperature between 15 and 25° C. The equivalent by weight of acetate added is preferentially three times greater than the weight of quaternary ammonium salt of the benzyl ester of the heparin used in the depolymerization reaction.

The saponification (step f) is generally carried out by means of an alkaline metal hydroxide, such as sodium hydroxide, potassium hydroxide or lithium hydroxide, in an aqueous medium, at a temperature between 0 and 20° C. and preferably between 0 and 10° C. From 1 to 5 molar equivalents of alkali metal hydroxide are generally used. Preferably, the saponification is carried out in the presence of from 1 to 2 molar equivalents of alkali metal hydroxide.

The purification (step g) can be carried out by means of hydrogen peroxide, in an aqueous medium, at a temperature of from 10 to 50° C. Preferably, this operation is carried out at between 20 and 40° C.

This process makes it possible to obtain semuloparin, having the following characteristics: an average molecular weight of 2000-3000 Daltons, an anti-FXa activity of approximately 160 U/mg and an anti-FIIa activity of approximately 2 U/mg. By virtue of its particularly low average molecular weight, such a product is referred to as ultra-low-molecular-weight heparin (ULMWH).

The anti-FXa and anti-FIIa activities mentioned above for semuloparin are measured by means of amidolytic methods on a chromogenic substrate, that are adapted from the monograph on LMWHs of the European Pharmacopoeia in force, using, as reconstitution buffer, a tris-NaCl buffer, pH 7.4, containing PEG 6000 (polyethylene glycol 6000) instead of albumin, and a reference ULMWH substance having an anti-FXa activity of 159 U/mg and an anti-FIIa activity of 2.9 U/mg. The activities are expressed in units per mg by virtue of the use of a ULMWH internal standard. Indeed, depending on the concentration/dilution, a lack of parallelism may be observed during the routine determination of anti-FIIa activities when the ULMWH is calibrated versus the LMWH standard. The anti-FXa and anti-FIIa activities of the reference ULMWH were defined relative to the standard International standard for low-molecular-weight heparins in a dilution range for which the parallelism is obtained. The results of the assays are exploited according to §5.3 of the European Pharmacopoeia in force ("Statistical analysis of results of biological assays and tests").

EXAMPLE 2

Preparation of the Dodecasaccharide (III)

In a first step, AVE5026 is fractionated by GPC on a column packed with Bio Gel P30 (200×5 cm) (2 g per injection). The dodecasaccharide fraction, which represents approximately 6 to 11% of the product, is gathered and is desalted on a column packed with Sephadex G10 (100×7 cm). It is recommended at this point to have at least 5 g of dodecasaccharide fraction as a starting base. In a second step, the fraction is entirely injected onto an ATIII affinity column (30×5 cm), using a step-gradient of NaCl concentration (0.7; 1.15; 1.6; 2.05; 2.65 and 3 M of NaCl in 1 mM Tris-HCl, pH 7.4). 200 mg are injected at each run, i.e. an overcapacity relative to the ATIII column. The fractions eluted for conductivities between 80 and 130 mS/cm, which are enriched in dodecasaccharide of formula (III), are gathered together. These fractions are desalted and purified in the next step on semi-preparative CTA-SAX columns (250×22 mm). The fractions are tested by analytical AS11 or CTA-SAX. After neutralization of the pH, the fractions gathered are run over a Mega Bond Elut C18 cartridge (Varian) before the final purification on a semi-preparative AS11 column (Dionex). The fractions containing the pure dodecasaccharide (III) are gathered together and desalted on Sephadex G10.

$^1$H NMR in $D_2O$ (δ in ppm): 2.05 (6H, s), 3.25 (2H, dd), 3.39 (2H, t, 8 Hz), 3.45 (2H, d, 10 Hz), between 3.60 and 4.55 (49H, m), 4.61 (2H, d, 7 Hz), 4.75 (1H, s), 4.80 (1H, s), 4.84 (1H, s), 5.02 (1H, s), 5.18 (3H, m), 5.35 (1H, broad d), 5.40 (1H, d, 2 Hz), 5.42 (1H, d, 2 Hz), 5.46 (1H, d, 2 Hz), 5.55 (2H, m), 5.81 (1H, d, 4 Hz).

EXAMPLE 3

Preparation of the Tetradecasaccharide (IV)

The first step of fractionation by GPC is carried out as in Example 2. The tetradecasaccharide fraction gathered at the end of the fractionation represents approximately 3 to 7% of the starting product and is then desalted as indicated in Example 2. In a second step, the fraction is entirely injected onto an ATIII affinity column, as indicated in example 2. The fractions enriched in tetradecasaccharide of formula (IV), eluted at conductivities between 100 and 130 mS/cm, are gathered. In the next step, the fractions are desalted and purified on a semi-preparative AS11 column (Dionex), by injecting 20 mg per run. The fractions are tested by analytical CTA-SAX. The fractions containing the pure tetradecasaccharide (IV) are gathered and desalted on Sephadex G10. The fractions are then injected onto a CTA-SAX column (150×10 mm) (3 μm). The fractions are tested, neutralized, and then run over a Bond Elut C18 cartridge (Varian) before the final purification on a semi-preparative AS11 column (Dionex). The eluates containing the pure tetradecasaccharide (IV) are gathered and desalted on Sephadex G10.

$^1$H NMR in $D_2O$ (δ in ppm): 2.04 (3H, s), 2.05 (3H, s), 3.27 (3H, m), 3.37 (2H, t, 8 Hz), 3.44 (2H, d, 10 Hz), between 3.60 and 4.55 (57H, m), 4.60 (2H, d, 7 Hz), 4.76 (1H, m), 4.79 (3H, m), 5.00 (1H, s), 5.15 (1H, d, 6 Hz), 5.18 (2H, m), 5.21 (1H, m), 5.33 (1H, broad d), 5.39 (1H, d, 3 Hz), 5.41 (1H, d, 3 Hz), 5.43 (1H, d, 3 Hz), 5.44 (1H, d, 3 Hz), 5.51 (2H, m), 5.80 (1H, d, 4 Hz).

EXAMPLE 4

Preparation of the Tetradecasaccharide (V)

The first step of fractionation by GPC is carried out as in example 2. The tetradecasaccharide fraction gathered at the end of the fractionation represents approximately 3 to 7% of the starting product and is then desalted as indicated in example 2. In a second step, the fraction is entirely injected onto an ATIII affinity column, as indicated in example 2. The fractions enriched in tetradecasaccharide of formula (V), eluted at conductivities between 100 and 130 mS/cm, are gathered. In the next step, these fractions are desalted and purified on a semi-preparative AS11 column (Dionex), by injecting 20 mg per run. The fractions are tested by analytical CTA-SAX. The fractions containing the pure tetradecasaccharide (V) are gathered and desalted on Sephadex G10. The fractions are then injected onto a CTA-SAX column (150×10 mm) (3 µm). The fractions are tested, neutralized, then run over a Bond Elut C18 cartridge (Varian) before the final purification on a semi-preparative AS11 column (Dionex). The eluates containing the pure tetradecasaccharide (V) are gathered and desalted on Sephadex G10.

$^1$H NMR in $D_2O$ (δ in ppm): 2.04 (3H, s), 2.05 (3H, s), 3.27 (3H, m), 3.37 (2H, t, 8 Hz), 3.44 (2H, d, 10 Hz), between 3.60 and 4.55 (57H, m), 4.60 (2H, d, 7 Hz), between 4.75 and 4.80 (4H, m), 5.01 (1H, s), 5.15 (1H, d, 6 Hz), 5.18 (2H, m), 5.22 (1H, m), 5.33 (1H, broad d), between 5.38 and 5.42 (3H, m), 5.44 (1H, d, 3 Hz), 5.50 (1H, d, 3 Hz), 5.52 (1H, d, 3 Hz), 5.80 (1H, d, 4 Hz).

EXAMPLE 5

Preparation of the Tetradecasaccharide (VI)

The first step of fractionation by GPC is carried out as in example 2. The tetradecasaccharide fraction gathered at the end of the fractionation represents approximately 3 to 7% of the starting product and is then desalted as indicated in example 2. In a second step, the fraction is entirely injected onto an ATIII affinity column, as indicated in example 2. The fractions enriched in tetradecasaccharide of formula (VI), eluated at conductivities between 100 and 130 mS/cm, are gathered. In the next step, these fractions are desalted and purified on a semi-preparative AS11 column (Dionex), by injecting 20 mg per run. The fractions are tested by analytical CTA-SAX. The fractions containing the pure tetradecasaccharide (VI) are gathered and desalted on Sephadex G10. The fractions are then injected onto a CTA-SAX column (150×10 mm) (3 µm). The fractions are tested, neutralized, and then run over a Bond Elut C18 cartridge (Varian) before the final purification on a semi-preparative AS11 column (Dionex). The eluates containing the pure tetradecasaccharide (VI) are gathered and desalted on Sephadex G10.

$^1$H NMR in $D_2O$ (δ in ppm): 2.03 (3H, s), 2.04 (3H, s), 2.05 (3H, s), 3.26 (2H, m), 3.37 (2H, t, 8 Hz), 3.44 (2H, d, 10 Hz), between 3.60 and 4.55 (58H, m), 4.60 (2H, d, 7 Hz), between 4.75 and 4.80 (4H, m), 5.00 (1H, s), 5.02 (1H, s), 5.15 (1H, d, 6 Hz), 5.18 (2H, m), 5.20 (1H, m), 5.33 (2H, m), 5.38 (1H, d, 3 Hz), 5.41 (1H, d, 3 Hz), 5.51 (2H, m), 5.80 (1H, d, 4 Hz).

In examples 2 to 5, the GPC step makes it possible to separate the dodecasaccharide and tetradecasaccharide fractions (fractionation according to the chain size). The CTA-SAX step then makes it possible to isolate the polysaccharides targeted and to distinguish polysaccharides of identical size through identification of the eluted compounds by analytical HPLC monitoring, according to the methodology described in Analytical Biochemistry, 2004, 332, 299-313, or else by $^1$H NMR monitoring. In particular, FIG. 5 represents the chromatographic separation by analytical CTA-SAX of the tetradecasaccharide fraction obtained after GPC, ATIII chromatography and anion exchange chromatography according to examples 3, 4 and 5 above. The thin-line signal corresponds to the UV detection at 234 nm, and the thick-line signal corresponds to the detection at the dual wavelengths 202-242 nm. The x-axes represent the time (in minutes) and the y-axes represent the UV absorbance (mAU: one-thousandth Absorbance Unit). The chromatographic separation and the analysis of the eluate are carried out under the conditions described by Mourier, P. A. J. and Viskov, C. in Analytical Biochemistry, 2004, 332, 299-313.

EXAMPLE 6

Quantification of the Dodecasaccharide (III)

The quantification of the dodecasaccharide (III) according to the invention was carried out on various samples of semuloparin. The contents of total dodecasaccharide fraction having affinity for ATIII and of dodecasaccharide of formula (III) are given in Table 1.

TABLE 1

Contents of dodecasaccharide fraction and of dodecasaccharide (III)

| Samples | Dodecasaccharides having affinity for ATIII (% in the dodecasaccharide fraction) | Dodecasaccharide (III) (ΔIIaIsIsIIaIsIs) (% area relative to the dodecasaccharide fraction having affinity) |
|---|---|---|
| N° 1 | 39.0 | 1.69 |
| N° 2 | 41.8 | 1.80 |
| N° 3 | 42.0 | 1.84 |
| N° 4 | 40.3 | 1.82 |
| N° 5 | 41.0 | 1.81 |
| N° 6 | 40.9 | 1.78 |
| N° 7 | 36.9 | 1.95 |
| N° 8 | 36.4 | 1.86 |
| N° 9 | 36.5 | 1.86 |
| N° 10 | 36.5 | 1.90 |
| N° 11 | 36.0 | 1.78 |
| N° 12 | 35.9 | 2.11 |

These dodecasaccharide (III) quantifications were calculated according to the detailed protocol which follows.

6.1: Isolation of Dodecasaccharide Fractions by GPC

Column: 100×2.6 cm, stationary phase Bio Gel P30 fine (Bio Rad).

Mobile phase: 0.2 mol/l $NaClO_4$; flow rate: 0.6 ml/min.

UV detection: Shimadzu SPD20A detector with dual detection at 232 nm and 202 nm.

Injection: 165 mg of semuloparin diluted in approximately 1 to 2 ml of mobile phase. For the injection, a Rheodyne valve with a 5 ml loop is used.

The total separation lasts approximately 700 min. Three injections of 165 mg are carried out for each batch. The collection is carried out on a Shimadzu collector. A chromatogram of the separation of sample No 3 (cf. table 1) is represented in FIG. 6 (thin line: detection at 232 nm; bold line: detection at 202 nm). The peak of the dodecasaccharide fraction is indicated with an arrow.

The dodecasaccharide fractions of the three separations are gathered and are desalted on a Sephadex G10 column (40×5 cm). Between 25 and 50 mg of dodecasaccharide fraction are thus isolated.

6.2: Antithrombin (AT) Affinity Chromatography of the Dodecasaccharide Fraction

This second step has a dual objective: to purify, from the fraction isolated, a sufficient amount of affinity dodecasaccharide fraction to carry out a quantification of the double site and, furthermore, to measure the percentage of the affinity fraction in the purified dodecasaccharide fraction.

The preparative part, which consists in purifying the affinity fraction, is carried out on a Sepharose AT column (30×7 cm) grafted with 2 g of human antithrombin. This chromatography column is prepared according to the teachings of patent application WO 2007/012754. The affinity column is stored at 4° C. Dual detection is used to monitor the separation: the UV wavelength at 232 nm and a conductimetric detection for monitoring the NaCl elution. The elution gradient is a simple step gradient. The mobile phase used is the following:

Solvent A: 0.25 M NaCl; 1 mM Tris, pH 7.4
Solvent B: 3.5 M NaCl; 1 mM Tris, pH 7.4
Gradient: t0 min, %B=0; t100 min, %B=100; t130 min, %B=100; t>196 min, %B=0
Flow rate: 12 ml/min
Analysis time: 310 min.

The dodecasaccharide fraction purified in the preceding phase is chromatographed on the preparative affinity column in two injections. An example of a chromatogram of a dodecasaccharide fraction is given in FIG. 7, corresponding to sample No 2 (cf. table 1). The thin line corresponds to the UV detection at 232 nm, and the bold line corresponds to the conductivity (mS/cm).

The affinity and non-affinity fractions resulting from the two injections are gathered and then desalted. The non-affinity fraction is run on a Q Sepharose Fast Flow column (20×2.6 cm), rinsed with water. The non-affinity fraction is completely retained on the column. The elution is carried out with a 1N $NaClO_4$ solution. The detection is carried out under UV at 232 nm and by conductimetry. The affinity fractions are reconcentrated in the same way by diluting them beforehand in 5 liters of water, and then by injecting them onto a Q Sepharose Fast Flow column (20×1.6 cm). The final desalting is carried out on a Sephadex G10 column (25×5 cm), with, as eluent, water injected at 10 ml/min. The desalted fractions are reconcentrated on a rotary evaporator and diluted in a 1.6 ml HPLC vial. The pH is tested and adjusted to between 5 and 7.

In order to determine the percentage of components having affinity for ATIII in the dodecasaccharide fraction, the percentage surface (area) of the peak of the affinity compounds on the affinity chromatography, after subtraction of a blank run, is measured. This percentage is determined on the two chromatograms obtained by preparative affinity chromatography, but also on three chromatograms from injection of the same fraction on an analytical Sepharose AT affinity column.

The analytical column is packed with the same phase as the preparative column and has the geometry 40×1.5 cm. The analytical conditions are the following:

Solvent A: 0.25 M NaCl; 1 mM Tris, pH 7.4
Solvent B: 3 M NaCl; 1 mM Tris, pH 7.4
Gradient: t0 min %B=0; t75 min %B=100; t90 min %B=100; t>91 min %B=0
Flow rate: 1 ml/min.

The amounts injected are much smaller than on the preparative column, typically 1 mg of dodecasaccharide. The percentage of affinity compounds is determined on the chromatogram at 232 nm according to the same method as that described for the preparative chromatography.

The percentages given for each sample are the average of the five determinations carried out on the preparative (×2) and analytical (×3) column. The results obtained are collected in table 1 above.

6.3: Quantification of the Double Site in the Affinity Fractions

The double-site dodecasaccharide of formula (III) is quantified by means of a highly resolutive HPLC method, namely using a Waters Acquity BEH C18 1.7 μm (2.1×150 mm) UPLC (Ultra Performance Liquid Chromatography) column, with pentylamine and HFIP (hexafluoroisopropanol) mobile phases. The column temperature is adjusted to 60° C. The eluant phase is the following:

Phase A: 50 mmol/l HFIP, 15 mmol/l pentylamine in water.
Phase B: 25-75 v/v $H_2O$—$CH_3CN$ with 50 mmol/l HFIP and 15 mmol/l pentylamine.
Flow rate: 0.22 ml/min.
UV detection: 232 nm and 245 nm.

The chromatogram of an affinity fraction of semuloparin sample N° 5 (cf. table 1) is given in FIG. 8 (thin line: detection at 232 nm; thick line: detection at 245 nm). The peak of the double-site dodecasaccharide (III) is indicated with an arrow. This peak can be attributed to the dodecasaccharide (III) through the use of an internal standard of this product, obtained in isolated form according to example 2 above. Alternatively, the identification of the dodecasaccharide (III) peak can be determined by coupling the Acquity column with mass spectrometry, according to the teaching of C. Doneanu et al., in Analytical Chemistry, 2009, Vol. 81, 3485-3499. In mass spectrometry, the dodecasaccharide (III) is identified by its molecular mass at 3226 Da (protonated form).

The quantification of the double-site dodecasaccharide (III) is carried out by calculating the percentage surface area of the corresponding chromatography peak relative to the entire fraction, after subtraction of a blank run. An example of integration is given in FIG. 9 (sample N° 5, cf. table 1), in which the surface area of the peaks identified by 1, 2, 3 and 4 are respectively of 11.783, 306.934, 465.625 and 3871.65. By way of example, the results obtained on 12 samples of semuloparin are reported in table 1 above.

EXAMPLE 7

Pharmacology

The polysaccharides according to the invention were the subject of pharmacological tests for determining their antithrombotic properties and their value as therapeutically active substances.

Antithrombin Affinity:

The interaction of the dodecasaccharide (III) and of fondaparinux, as a reference compound, with antithrombin was studied by the fluorimetric titration method, according to the method described in Journal of Biological Chemistry, 2008, 283(39), 26662-266675. The results are summarized in table 2.

TABLE 2

| Dissociation constants (Kd), in μM | | | |
| --- | --- | --- | --- |
| | [NaCl] (M) | | |
| | 0.1 | 0.25 | 0.5 |
| Dodecasaccharide (III) | 0.0099 | 0.086 | 1.23 |
| Fondaparinux | 0.0207 | 0.279 | 3.47 |

These results show that the dodecasaccharide (III) has a greater affinity for antithrombin III than the reference compound, the pentasaccharide fondaparinux (synthetic pentasaccharide with specific activity towards factor Xa). Depending on the concentration tested, the dodecasaccharide (III) has 2.1 to 3.2 times more affinity for ATIII than fondaparinux. These results are surprising in that, in view of current knowledge, a single affinity site might have been expected to bind with the antithrombin III, and therefore the dodecasaccharide (III) might have been expected to exhibit a level of affinity of the same order of magnitude as that observed for fondaparinux. As it happens, these results imply that either the two affinity sites bind to ATIII, or that just one site binds, while the second site creates reinforcement of the binding. In any event, the dodecasaccharide (III) exhibits a strong affinity for antithrombin III.

Anti-FXa Activity in Plasma or in a Buffer Medium:

The anti-FXa activity of the dodecasaccharide (III) was determined with the ACL 7000 automated instrument for measuring coagulation (Instrumentation Laboratory), using the Heparin®-kit preparation (Instrumentation Laboratory) which contains antithrombin III, factor Xa and the chromogenic substrate S-2765. The measurements were carried out according to the manufacturer's recommendations. The 2nd low-molecular-weight heparin international standard (National Institute for Biological Standards and Control, London, UK, established in 2003, code no. 01/608) was used to construct the calibration curve. Enoxaparin (Clexane®) and fondaparinux (Arixtra®) were used as internal standard compounds.

The test samples or the 2nd LMWH international standard were first of all diluted in standard human plasma (Instrumentation Laboratory) or in a buffer (0.05 M Tris-HCl, 0.154 M NaCl, pH 7.4). The test solutions containing the samples in plasma or in the buffered medium are then diluted to 1:20 with a buffered solution containing the antithrombin and are placed in duplicate in the sites of the machine that are provided for this purpose. The factor Xa reagent and the chromogenic substrate are introduced into the reservoirs provided for this purpose in the ACL 7000 instrument. The anti-FXa activity test is carried out according to the "Heparin" program integrated into the user interface ("software") of the ACL 7000. During the assay, 50 µl of the sample diluted in the buffer are mixed with 50 µl of the factor Xa reagent. After an incubation time of 60 seconds at 37° C., 50 µl of chromogenic substrate (1.1 mM) are added and the changes in absorption are measured as a function of time at a wavelength of 405 nM. The anti-FXa activity of the samples tested was determined using a calibration curve constructed with the 2nd LMWH international standard (code No. 01/608).

The results are summarized in table 3.

TABLE 3

| Anti-FXa activities in values by mass | | |
|---|---|---|
| | Human plasma IU/mg | Tris buffer IU/mg |
| Dodecasaccharide (III) | 986.5 | 890.2 |
| Fondaparinux | 868.3 | 856.5 |
| Enoxaparin | 125.0 | 103.0 |

These results indicate a comparable anti-FXa activity by weight between the dodecasaccharide (III) and the pentasaccharide fondaparinux. However, on a molar basis, the dodecasaccharide according to the invention is twice as powerful as the fondaparinux reference, as indicated in table 4 (respective molar masses of fondaparinux and of the dodecasaccharide (III) in the form of sodium salts: 1728 and 3668 g/mol).

TABLE 4

| Anti-FXa activities in molar values | | |
|---|---|---|
| | Human plasma IU/µmol | Tris buffer IU/µmol |
| Dodecasaccharide (III) | 3618 | 3265 |
| Fondaparinux | 1500 | 1480 |

The same conclusions can be deduced with respect to the hexasaccharide sequence alone (sequence CDEFGF defined above): since its anti-FXa activity is about 800 IU/mg, the dodecasaccharide according to the invention exhibits an anti-FXa activity that is twice as high when this activity is reported on a molar basis.

Likewise, for the tetradecasaccharides of the present invention, the molar anti-FXa activity is higher, by about a factor of 2, compared with that of the pentasaccharide fondaparinux (cf. table 5).

For the tetradecasaccharides according to the invention, the protocol for measuring the anti-FXa activity was determined in vitro by means of an assay which determines the ability of the compound to accelerate the inhibition of factor Xa by antithrombin III. The International Units for the anti-FXa activity correspond to the activities of a given amount of the international standard of the substance to be examined. The low-molecular-weight heparin (BRP: Biology Reference Preparation) as listed in the European Pharmacopoeia, calibrated in International Units by comparison with the 2nd international standard (cf. previously), serves as a reference preparation. Two independent series of four dilutions of the reference solution and of the substance to be examined are prepared in a tris(hydroxymethyl)aminomethane-sodium chloride buffer solution, pH 7.4. The dilutions are chosen so as to obtain a linear response when the absorbance is expressed as a function of the logarithm of the concentration. 20 µl of the dilutions of the reference preparation and of the substance to be examined are deposited in a microplate and mixed with 20 µl of antithrombin III solution. After an incubation time of 60 seconds, 40 µl of bovine factor Xa solution are added. After incubation for 60 seconds, 100 µl of chromogenic substrate are added. The reaction is stopped after 4 minutes with 100 µl of acetic acid. The absorbance is measured at a wavelength of 405 nm. The anti-FXa activity is calculated using the customary conditions of statistical analysis for parallel on-line titrations, described in §5.3 of the European Pharmacopoeia. The activity of the substance to be examined is expressed in International Units of anti-FXa activity per mg on an unmodified basis (without correction with respect to the loss of water content).

TABLE 5

Anti-FXa activities of the tetradecasaccharides, in a Tris buffer medium

| | Molecular weight | Anti-FXa activities | |
|---|---|---|---|
| | (sodium salts) (g/mol) | Values by mass (U/mg) | Molar values (U/µMol) |
| Tetradecasaccharide (IV) | 4334 | 537.2 | 2328 |
| Tetradecasaccharide (V) | 4334 | 684.1 | 2964 |
| Tetradecasaccharide (VI) | 4171 | 559.7 | 2334 |

Moreover, in comparison with enoxaparin, the LMWH most widely used in therapy to date (sold under the name Lovenox® or Clexane® by Sanofi-Aventis), the dodecasaccharide (III) and the tetradecasaccharides (IV), (V) and (VI) according to the invention are much more powerful on factor Xa (cf. tables 3 and 5). The same is true with respect to AVE5026, the starting ULMWH from which the polysaccharides according to the invention are derived (cf. example 1 above).

The compounds according to the invention are therefore surprising both from the point of view of their chemical structure (presence of two ATIII-binding sites) and from the point of view of their pharmacological properties (very high anti-FXa activity, more stronger affinity towards ATIII than that of the reference compound fondaparinux).

By virtue of their powerful antithrombotic properties, the polysaccharides according to the invention can therefore be used for preparing medicaments, in particular antithrombotic medicaments. Another subject of the invention is therefore a medicament which comprises a polysaccharide according to the present invention, in acid form or in the form of a pharmaceutically acceptable salt thereof.

Such a medicament is useful in therapy, in particular for treating and preventing thromboses, including vein and arterial thromboses, deep vein thrombosis and pulmonary embolism.

According to another of its aspects, the present invention relates to pharmaceutical compositions comprising a polysaccharide according to the invention as an active ingredient. These pharmaceutical compositions contain an effective dose of at least one compound according to the invention, or a pharmaceutically acceptable salt of said compound, and also at least one pharmaceutically acceptable excipient. Said excipients are chosen, according to the pharmaceutical form and the method of administration desired, from the usual excipients which are known to those skilled in the art.

The pharmaceutical compositions according to the invention can also comprise at least one other active ingredient chosen from antithrombotic oligosaccharides, whether they are synthetic (obtained by chemical synthesis from monosaccharide or oligosaccharide intermediates) or obtained by isolation from sources of heparins or of LMWHs.

In the pharmaceutical compositions of the present invention for oral, sublingual, subcutaneous, intramuscular, intravenous, topical, local, intratracheal, intranasal, transdermal or rectal administration, the active ingredient of formula (I) above, or salt thereof, can be administered in unit administration form, as a mixture with conventional pharmaceutical excipients, to animals and to human beings for preventing or treating the abovementioned pathological conditions.

According to another of its aspects, the present invention also relates to a method for treating and preventing the pathological conditions indicated above, which comprises the administration, to a patient, of an effective dose of a compound according to the invention, or a pharmaceutically acceptable salt thereof.

The invention claimed is:

1. A sulfonated polysaccharide having a polysaccharide of heparin which has a molecular weight of less than 8000 Daltons, said sulfonated polysaccharide comprising two antithrombin III-affinity sites, wherein said polysaacharide is in isolated form.

2. The polysaccharide according to claim 1, comprising two antithrombin III-binding hexasaccharide sequences.

3. The polysaccharide according to claim 2, wherein said polysaccharide twice comprises the antithrombin III-binding hexasaccharide sequence corresponding to formula (I):

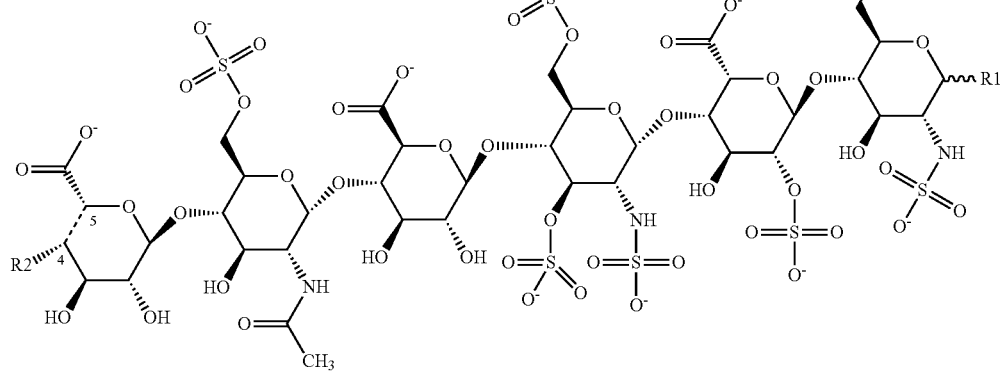

in which:
the bond represented as a dashed line between carbon atoms 4 and 5 of the first saccharide unit is either a single bond or a double bond, the wavy line denotes a bond located either below or above the plane of the pyranose ring of the glucosamine unit to which R1 is attached, R1 represents an OH group when the hexasaccharide of formula (I) is located at the reducing end of the polysaccharide, or else R1 represents a bond with another saccharide unit of said polysaccharide, in which case the bond is located above the plane of the pyranose ring of the glucosamine unit to which R1 is attached, R2 represents a hydrogen atom when the hexasaccharide of formula (I) is located at the non-reducing end of the polysaccharide, in which case the bond between carbon atoms 4 and 5 of the first saccharide unit of said hexasaccharide is a double bond, or else R2 represents a bond with another saccharide unit of said polysaccharide, in which case the bond between carbon atoms 4 and 5 of the first saccharide unit of said hexasaccharide is a single bond, said polysaccharide being in acid form or in salified form.

4. The polysaccharide according to claim 1 comprising between 12 and 22 saccharide units.

5. The polysaccharide according to claim 1 corresponding to formula

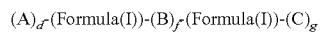

$(A)_d\text{-(Formula(I))-}(B)_f\text{-(Formula(I))-}(C)_g$      (II)

in which:
the A, B and C units, which may be identical to or different from one another, represent disaccharide sequences,
the units of formula (I) represent a hexasaccharide sequence corresponding to Formula (I):

in which:
the bond represented as a dashed line between carbon atoms 4 and 5 of the first saccharide unit is either a single bond or a double bond, the wavy line denotes a bond located either below or above the plane of the pyranose ring of the glucosamine unit to which R1 is attached, R1 represents an OH group when the hexasaccharide of formula (I) is located at the reducing end of the polysaccharide, or else R1 represents a bond with another saccharide unit of said polysaccharide, in which case the bond is located above the plane of the pyranose ring of the glucosamine unit to which R1 is attached, R2 represents a hydrogen atom when the hexasaccharide of formula (I) is located at the non-reducing end of the polysaccharide, in which case the bond between carbon atoms 4 and 5 of the first saccharide unit of said hexasaccharide is a double bond, or else R2 represents a bond with another saccharide unit of said polysaccharide, in which case the bond between carbon atoms 4 and 5 of the first saccharide unit of said hexasaccharide is a single bond, said polysaccharide being in acid form or in salified form, the subscripts d, f and g each represent an integer equal to 0 or comprised between 1 and 5, on the condition that the sum of the integers d, f and g is comprised between 0 and 5.

6. The polysaccharide according to claim 1 corresponding to formula (II):

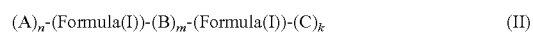

$(A)_n\text{-(Formula(I))-}(B)_m\text{-(Formula(I))-}(C)_k$      (II)

in which:
the A, B and C units, which may be identical to or different from one another, represent disaccharide sequences,
the units of formula (I) represent a hexasaccharide sequence corresponding to formula (I):

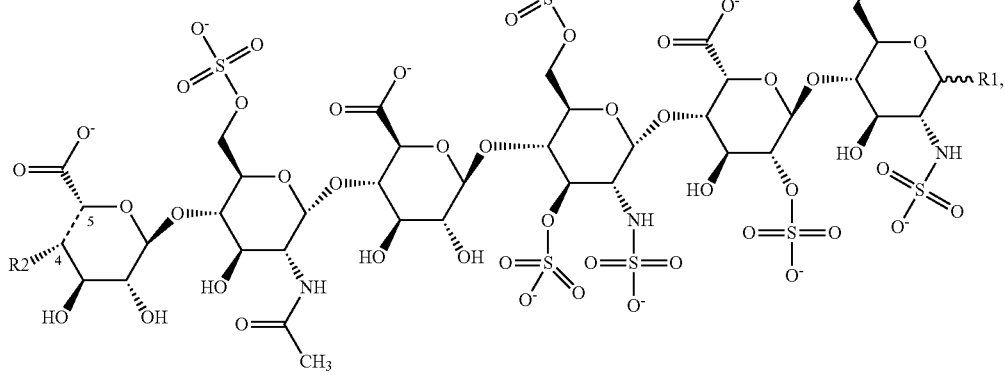

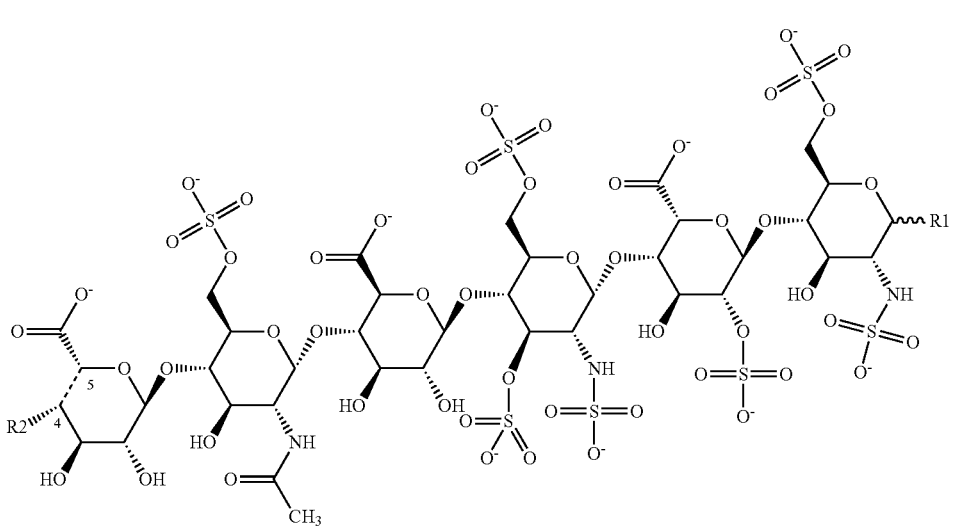

(I)

in which:

the bond represented as a dashed line between carbon atoms 4 and 5 of the first saccharide unit is either a single bond or a double bond, the wavy line denotes a bond located either below or above the plane of the pyranose ring of the glucosamine unit to which R1 is attached, R1 represents an OH group when the hexasaccharide of formula (I) is located at the reducing end of the polysaccharide, or else R1 represents a bond with another saccharide unit of said polysaccharide, in which case the bond is located above the plane of the pyranose ring of the glucosamine unit to which R1 is attached, R2 represents a hydrogen atom when the hexasaccharide of formula (I) is located at the non-reducing end of the polysaccharide, in which case the bond between carbon atoms 4 and 5 of the first saccharide unit of said hexasaccharide is a double bond, or else R2 represents a bond with another saccharide unit of said polysaccharide, in which case the bond between carbon atoms 4 and 5 of the first saccharide unit of said hexasaccharide is a single bond, said polysaccharide being in acid form or in salified form, the subscripts n, m and k each represent an integer equal to 0 or to 1, on the condition that, when one of the subscripts n, m or k is equal to 1, then the other two subscripts are equal to 0.

7. The polysaccharide according to claim 1 comprising 12 saccharide units and corresponding to formula (III):

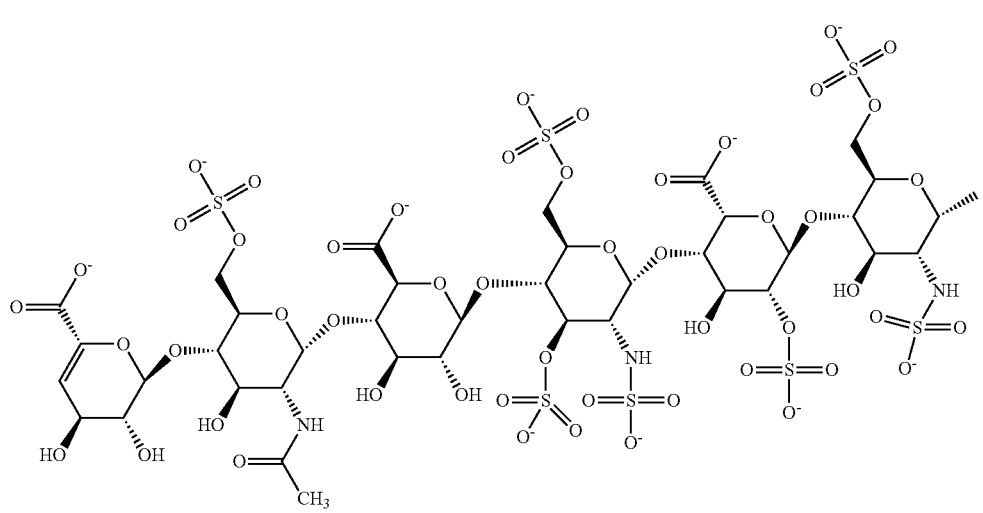

(III)

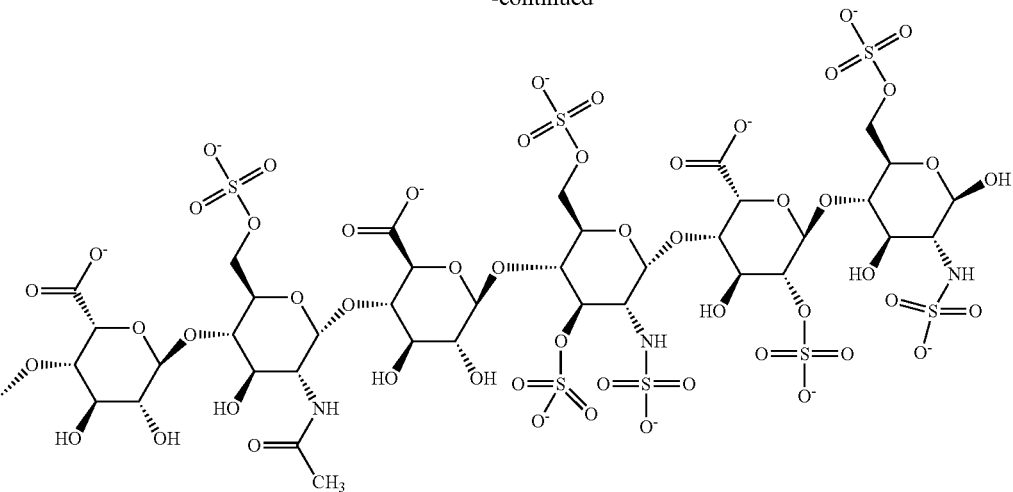
said polysaccharide being in acid form or in salified form.
8. The polysaccharide according to claim 1 comprising 14 saccharide units.
9. The polysaccharide according to claim 8, corresponding to formulae (IV), (V) or (VI):
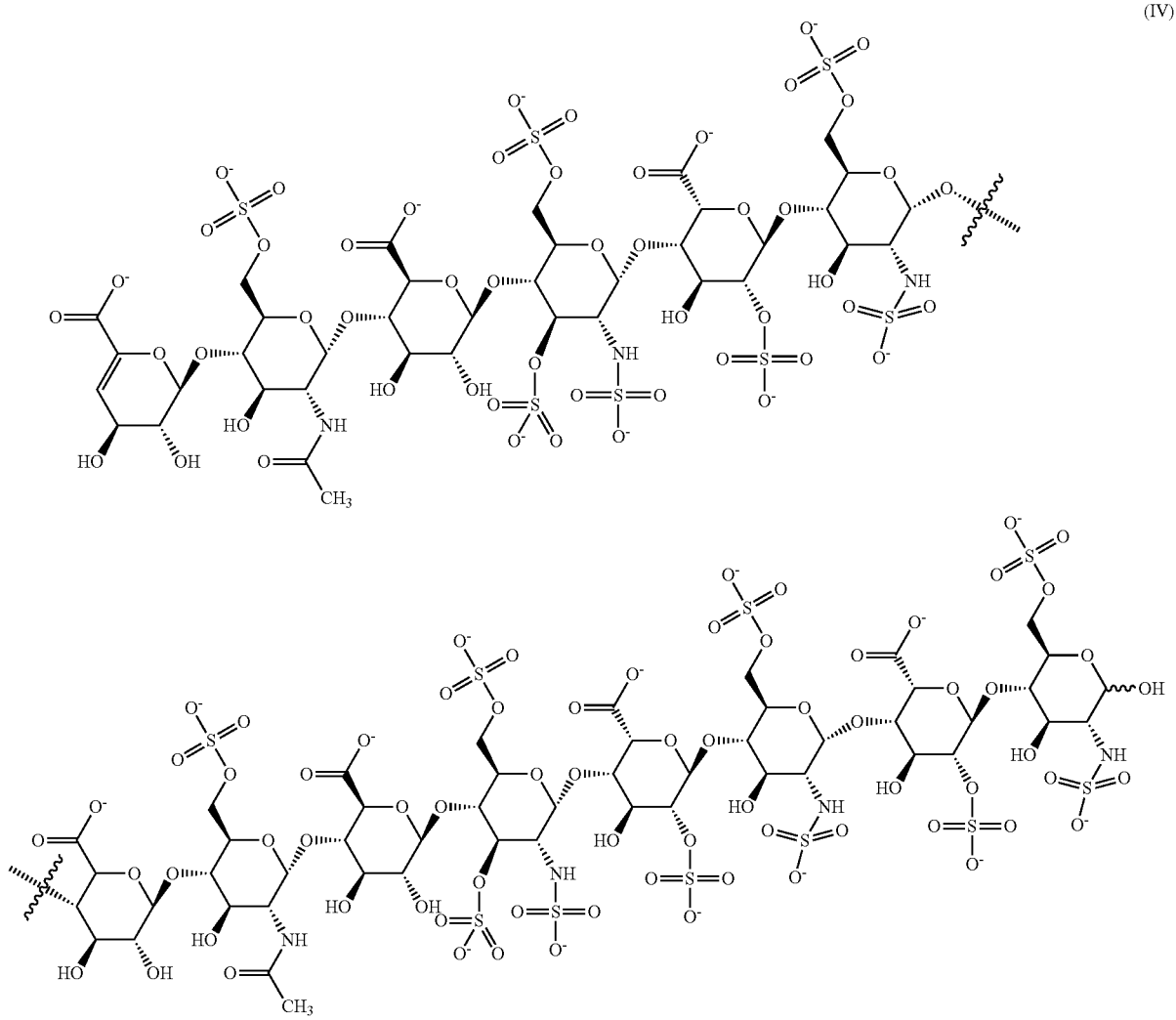
(IV)

(V)
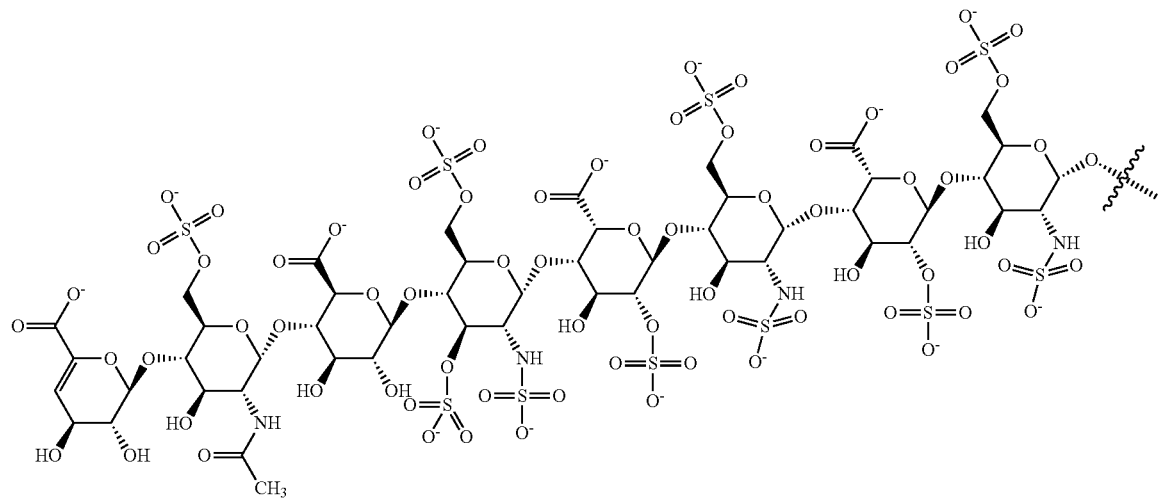
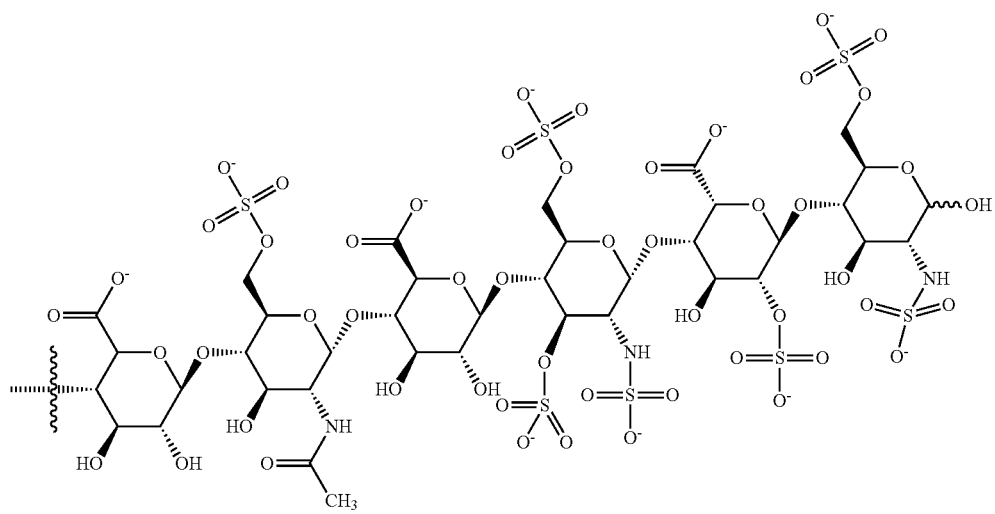
(VI)
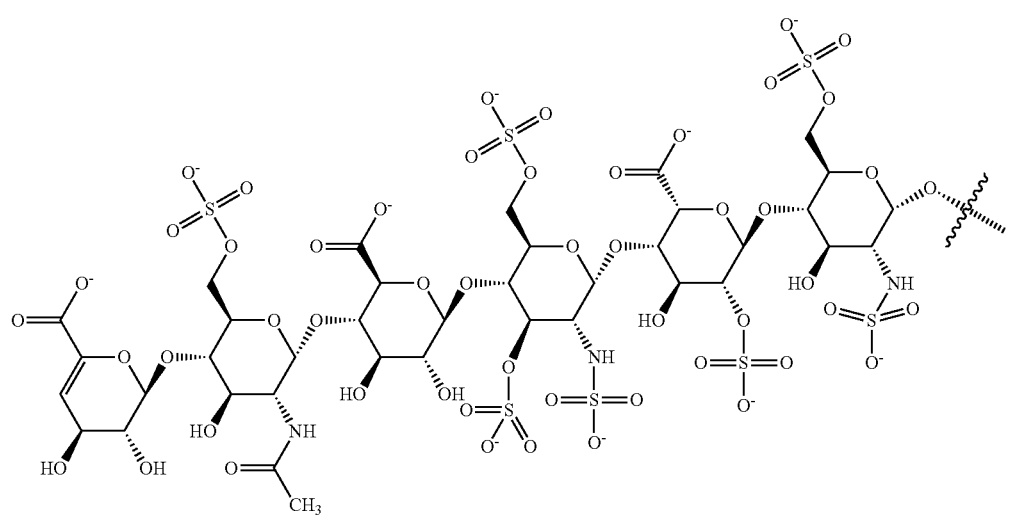

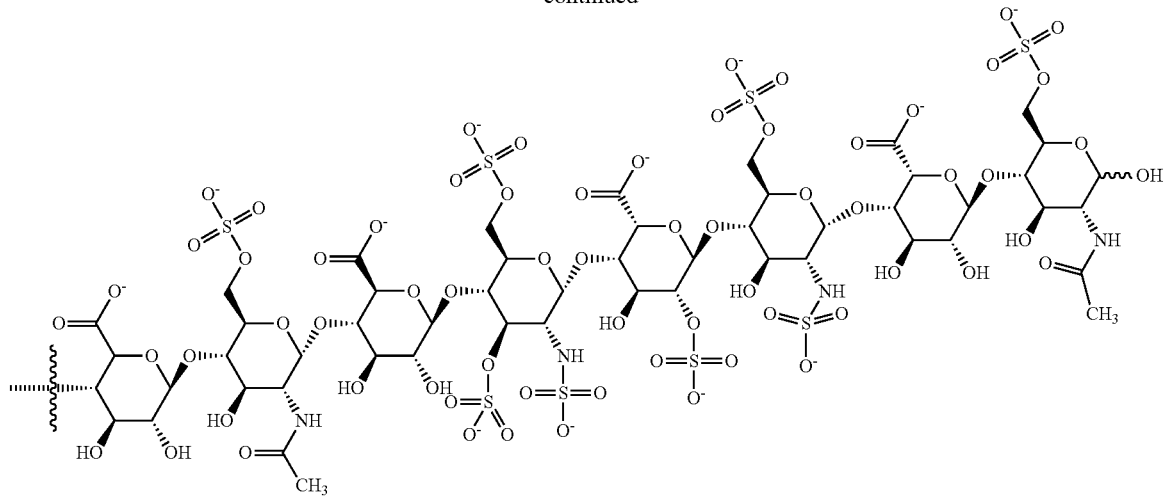

in which the wavy line denotes a bond located either below or above the plane of the pyranose ring of the glucosamine unit, said polysaccharide being in acid form or in salified form.

10. The polysaccharide according to claim 1, wherein said polysaccharide is in the form of a sodium salt.

11. A pharmaceutical composition, comprising the polysaccharide according to claim 1, or a pharmaceutically acceptable salt thereof, and at least one pharmaceutically acceptable excipient.

12. A method for treating thrombosis, comprising administering to a patient in need thereof a therapeutically effective amount of the polysaccharide of claim 1 or a pharmaceutically acceptable salt thereof.

13. The method of claim 12, wherein the thrombosis is selected from vein and arterial thromboses, deep vein thrombosis and pulmonary embolism.

14. A process for preparing the polysaccharide according to claim 1 comprising orthogonally seperating said polysaccharide from a low-molecular-weight or ultra-low-molecular-weight heparin, said separating comprising performing gel permeation, high performance liquid chromatography and AM affinity chromatography, combined with one another.

15. The process according to claim 14, wherein said process comprises the following steps:
gel permeation, then
ATIII-affinity chromatography, then
high performance liquid chromatography on a CTA-SAX column, then
purification by anion exchange chromatography and desalting by gel filtration.

16. The process according to claim 14, comprising the use of an ultra-low-molecular-weight heparin.

17. The process according to claim 16, wherein the ultra-low-molecular-weight heparin is semuloparin.

18. A method for analysing a sample of a heparin derivative comprising the following steps:
a) subjecting a test sample to orthogonal separation comprising orthogonally separating polysaccharides from the heparin, further comprising a step of isolating a dodecasaccharide fraction and/or the tetradecasaccharide fraction of said sample, and
b) quantifying the amount of one or more sulphated polysaccharides of formula (III), (IV), (V) or (VI)

(III)

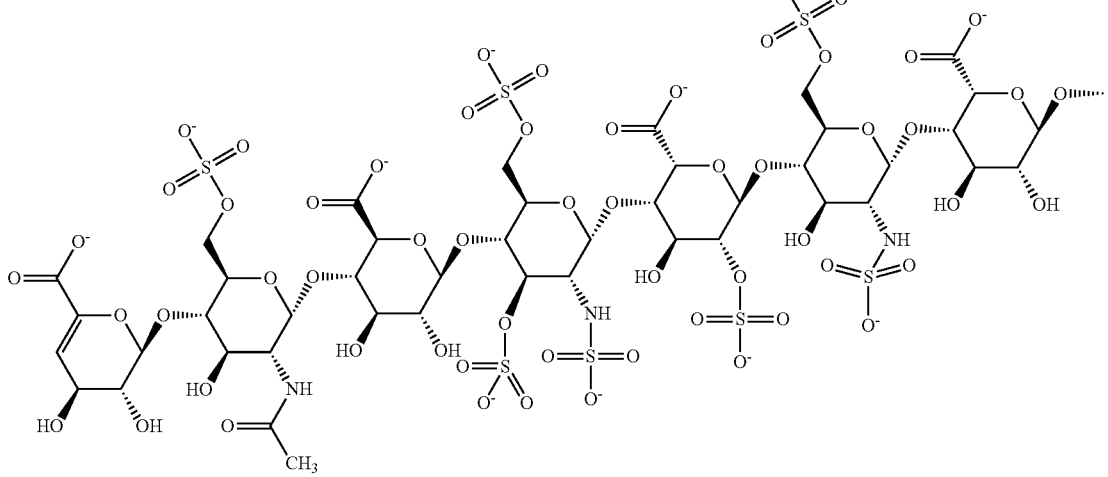

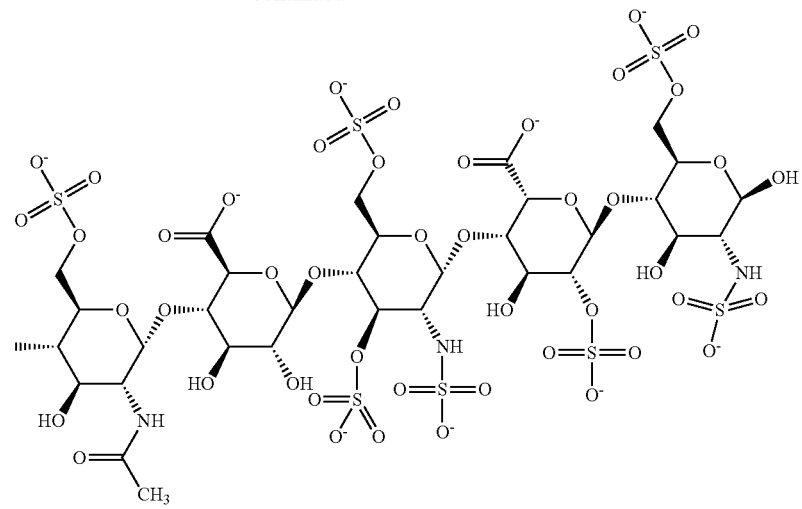
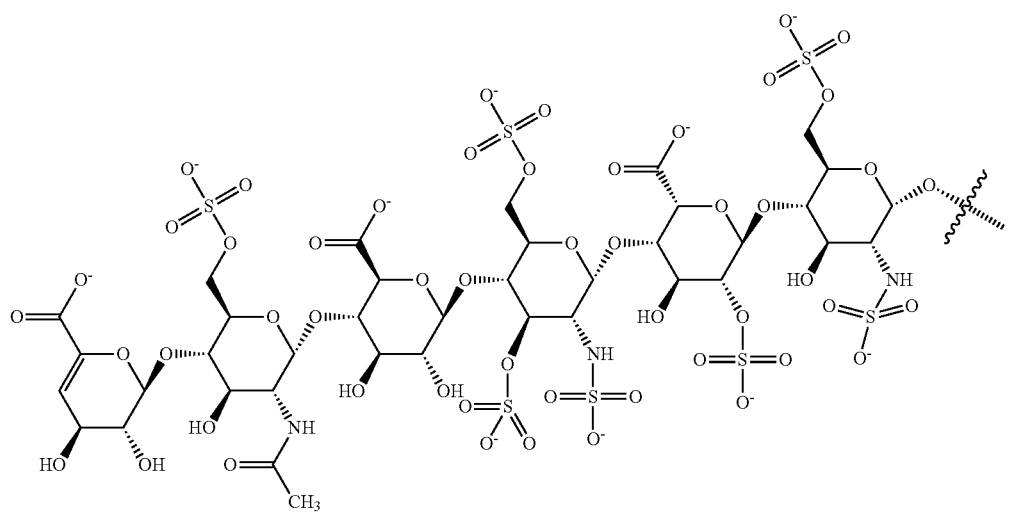
(IV)
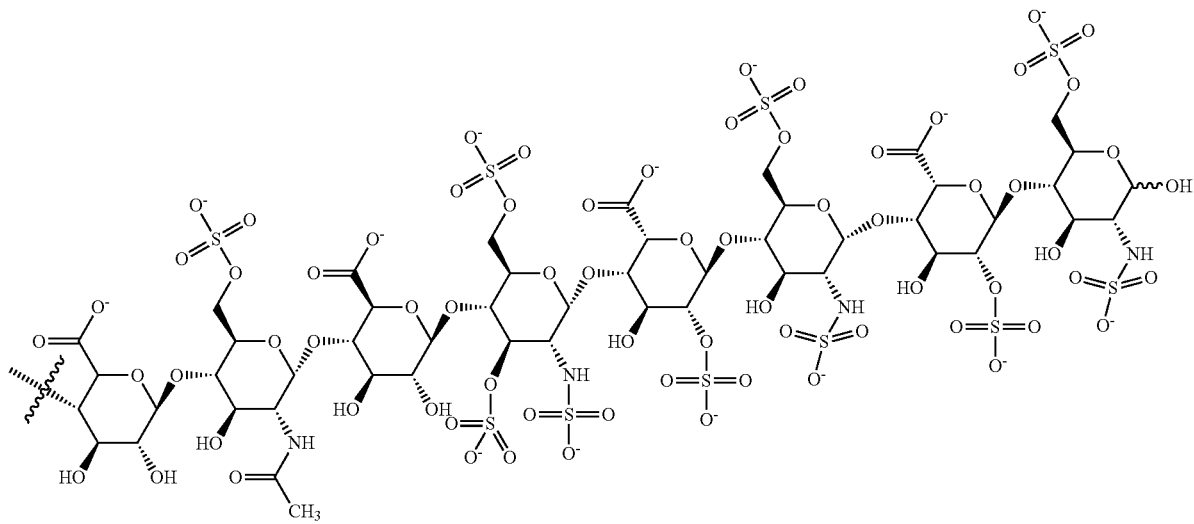

(V)
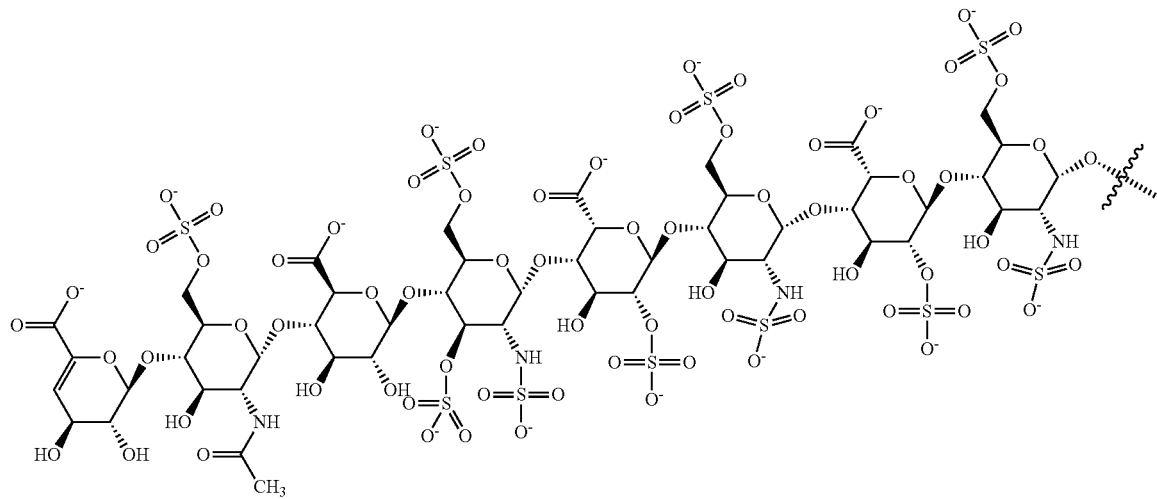
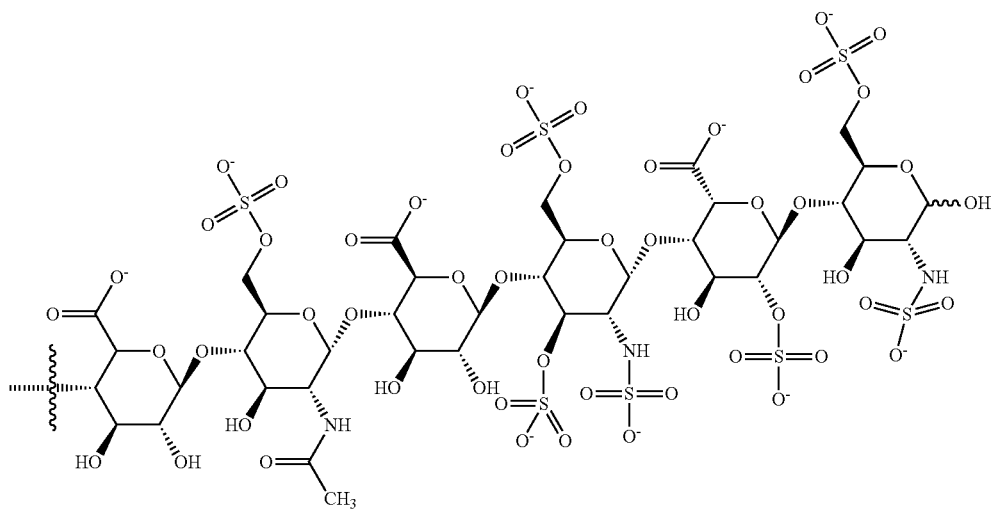
(VI)
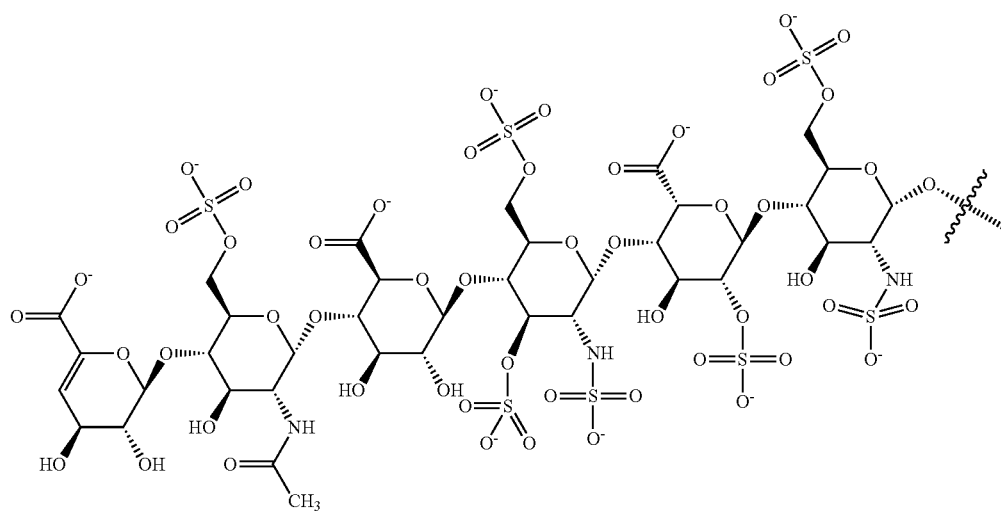

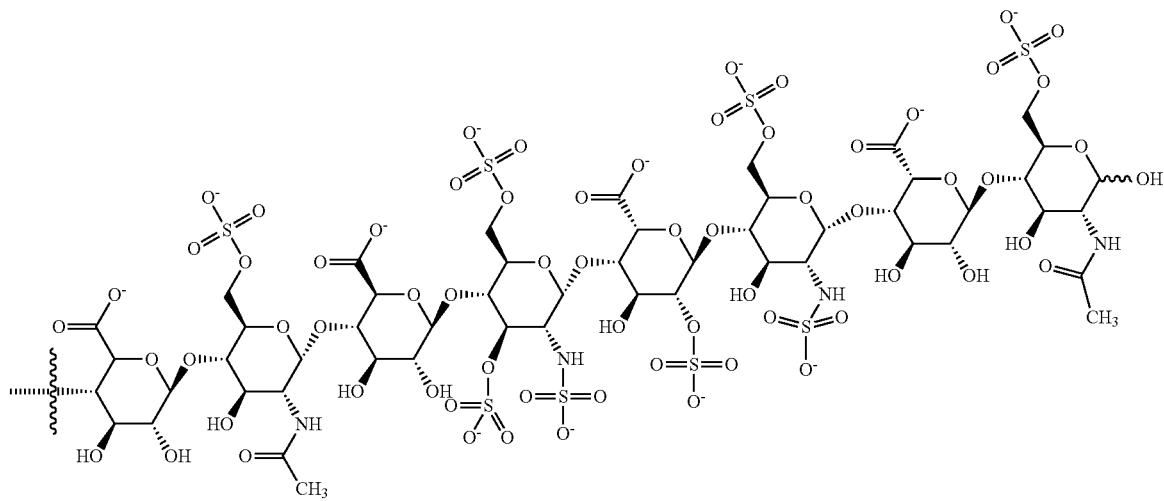

in said dodecasaccharide and/or tetradecasaccharide fractions.

19. The method of claim 18, wherein the heparin derivative comprises semuloparin.

20. A method for analysing a sample of a heparin derivative, comprising the following steps:
   a) subjecting a test sample to orthogonal separation comprising a step of orthogonally separating polysaccharides from the heparin, further comprising a step of isolating a dodecasaccharide fraction of said sample, and
   b) quantifying the amount of the sulphated polysaccharide of formula (III)

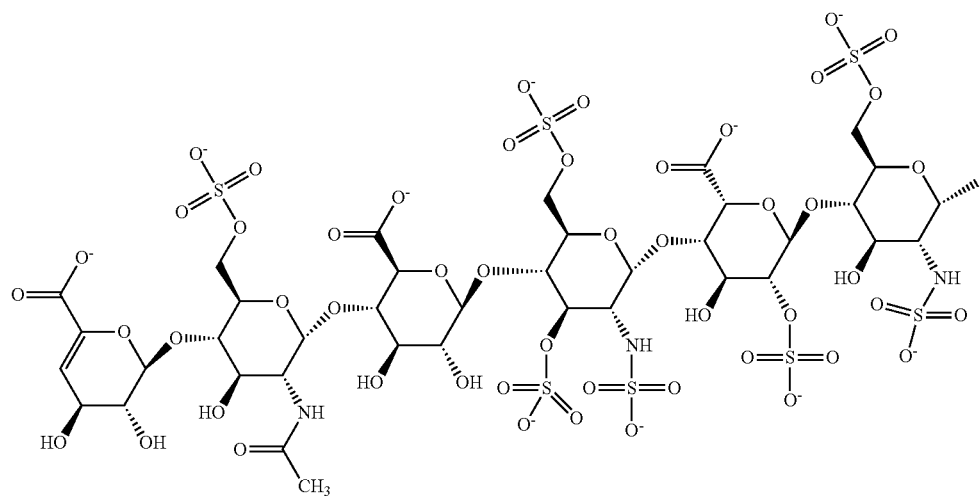

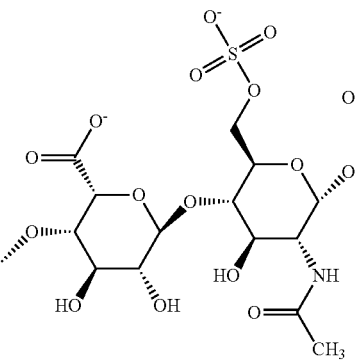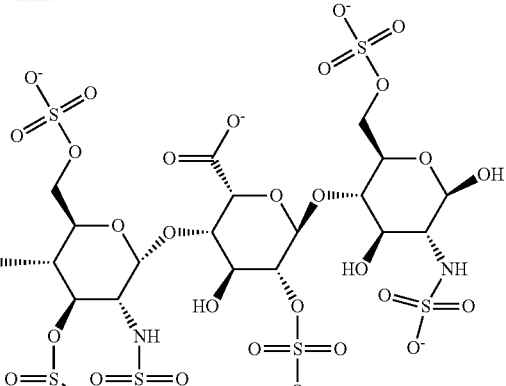
in said dodecasaccharide fraction.
21. The method of claim 20, wherein the heparin derivative comprises semuloparin.
* * * * *